(12) United States Patent  
Nau, Jr. et al.

(10) Patent No.: US 10,806,515 B2  
(45) Date of Patent: Oct. 20, 2020

(54) LIGHT ENERGY SEALING, CUTTING, AND SENSING SURGICAL DEVICE

(71) Applicant: Covidien LP, Mansfield, MA (US)

(72) Inventors: William H. Nau, Jr., Longmont, CO (US); Craig A. Keller, Boulder, CO (US); Duane E. Kerr, Loveland, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/011,960

(22) Filed: Jun. 19, 2018

(65) Prior Publication Data

US 2018/0296272 A1    Oct. 18, 2018

Related U.S. Application Data

(60) Continuation of application No. 15/912,899, filed on Mar. 6, 2018, which is a continuation of application (Continued)

(51) Int. Cl.
*A61B 18/28* (2006.01)
*A61B 17/29* (2006.01)
(Continued)

(52) U.S. Cl.
CPC .............. *A61B 18/28* (2013.01); *A61B 17/29* (2013.01); *A61B 18/1445* (2013.01);
(Continued)

(58) Field of Classification Search
CPC . A61B 18/18; A61B 2018/1807; A61B 18/20; A61B 2018/20361; A61B 18/22;
(Continued)

(56) References Cited

U.S. PATENT DOCUMENTS

D249,549 S    9/1978 Pike
4,143,660 A    3/1979 Malyshev et al.
(Continued)

FOREIGN PATENT DOCUMENTS

CN    201299462 Y    9/2009
DE    2415263 A1    10/1975
(Continued)

OTHER PUBLICATIONS

Int'l Search Report EP 06024123.9 dated Mar. 6, 2007.
(Continued)

*Primary Examiner* — Ahmed M Farah
(74) *Attorney, Agent, or Firm* — Carter, DeLuca & Farrell LLP

(57) ABSTRACT

The present disclosure is directed towards a medical instrument. The medical instrument includes a housing and an end effector assembly operably connected to the housing. The end effector assembly includes first and second jaw members each having a tissue contacting surface, at least one of the first and second jaw members movable between a first, spaced-apart position and a second proximate position, wherein in the second position, the jaw members cooperate to define a cavity configured to receive tissue between the jaw members. The end effector also includes at least one light-emitting element coupled to at least one of the first and second jaw members, the at least one light-emitting element adapted to deliver light energy to tissue grasped between the first and second jaw members to treat the tissue.

7 Claims, 19 Drawing Sheets

US 10,806,515 B2
Page 2

Related U.S. Application Data

No. 15/458,634, filed on Mar. 14, 2017, now Pat. No. 9,925,008, which is a continuation of application No. 15/191,697, filed on Jun. 24, 2016, now Pat. No. 9,610,121, which is a division of application No. 13/430,325, filed on Mar. 26, 2012, now Pat. No. 9,375,282.

(51) Int. Cl.

| | | |
|---|---|---|
| *A61B 18/22* | (2006.01) | |
| *A61B 18/14* | (2006.01) | |
| *A61B 18/18* | (2006.01) | |
| *A61B 18/20* | (2006.01) | |
| *A61B 18/00* | (2006.01) | |
| *A61B 17/00* | (2006.01) | |

(52) U.S. Cl.
CPC .............. *A61B 18/18* (2013.01); *A61B 18/22* (2013.01); *A61B 18/20* (2013.01); *A61B 2017/00057* (2013.01); *A61B 2018/0063* (2013.01); *A61B 2018/00184* (2013.01); *A61B 2018/00601* (2013.01); *A61B 2018/00642* (2013.01); *A61B 2018/1807* (2013.01); *A61B 2018/2055* (2013.01); *A61B 2018/20361* (2017.05); *A61B 2018/2253* (2017.05); *A61B 2018/2272* (2013.01); *A61B 2018/2277* (2013.01); *A61B 2018/2294* (2013.01)

(58) Field of Classification Search
CPC .... A61B 2018/2253; A61B 2018/2255; A61B 2018/2272; A61B 2018/2277; A61B 18/28; A61B 18/00; A61B 2018/00; A61B 2018/00053; A61B 2018/00184; A61B 2018/00571; A61B 2018/00589; A61B 2018/00601; A61B 2018/00607; A61B 2018/0063; A61B 2018/00636; A61B 2018/00642
USPC ...................................... 606/3, 16, 205–208
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| 4,757,425 A | 7/1988 | Waltz |
| D298,353 S | 11/1988 | Manno |
| D299,413 S | 1/1989 | DeCarolis |
| 5,037,433 A | 8/1991 | Wilk et al. |
| 5,055,983 A | 10/1991 | Hunold et al. |
| 5,147,356 A | 9/1992 | Bhatta |
| 5,169,396 A | 12/1992 | Dowlatshahi et al. |
| 5,209,748 A | 5/1993 | Daikuzono |
| 5,217,460 A | 6/1993 | Knoepfler |
| 5,258,006 A | 11/1993 | Rydell et al. |
| D343,453 S | 1/1994 | Noda |
| 5,318,589 A | 6/1994 | Lichtman |
| D348,930 S | 7/1994 | Olson |
| 5,349,341 A | 8/1994 | Lichtman et al. |
| 5,336,220 A | 8/1994 | Ryan et al. |
| 5,336,221 A | 8/1994 | Anderson |
| 5,342,358 A | 8/1994 | Daikuzono |
| 5,376,094 A | 12/1994 | Kline |
| D354,564 S | 1/1995 | Medema |
| 5,383,880 A | 1/1995 | Hooven |
| D358,887 S | 5/1995 | Feinberg |
| 5,415,657 A | 5/1995 | Taymor-Luria |
| 5,569,241 A | 10/1996 | Edwards |
| D384,413 S | 9/1997 | Zlock et al. |
| 5,762,609 A * | 6/1998 | Benaron .............. A61B 5/0084 600/473 |
| H1745 H | 8/1998 | Paraschac |
| 5,800,449 A | 9/1998 | Wales |
| 5,807,393 A | 9/1998 | Williamson, IV et al. |
| 5,827,281 A | 10/1998 | Levin |
| 5,827,323 A | 10/1998 | Klieman et al. |
| D402,028 S | 12/1998 | Grimm et al. |
| 5,849,022 A | 12/1998 | Sakashita et al. |
| 5,868,760 A | 2/1999 | McGuckin, Jr. |
| D408,018 S | 4/1999 | McNaughton |
| 5,921,916 A | 7/1999 | Aeikens et al. |
| 5,957,937 A | 9/1999 | Yoon |
| D416,089 S | 11/1999 | Barton et al. |
| 5,993,466 A | 11/1999 | Yoon |
| 5,993,467 A | 11/1999 | Yoon |
| 6,004,332 A | 12/1999 | Yoon et al. |
| 6,024,741 A | 2/2000 | Williamson, IV et al. |
| 6,039,729 A | 3/2000 | Durville et al. |
| 6,053,909 A | 4/2000 | Shadduck |
| 6,053,933 A | 4/2000 | Balazs et al. |
| D424,694 S | 5/2000 | Tetzlaff et al. |
| D425,201 S | 5/2000 | Tetzlaff et al. |
| 6,086,601 A | 7/2000 | Yoon |
| H1904 H | 10/2000 | Yates et al. |
| 6,126,665 A | 10/2000 | Yoon |
| 6,143,005 A | 11/2000 | Yoon et al. |
| 6,224,614 B1 | 5/2001 | Yoon |
| 6,283,961 B1 | 9/2001 | Underwood et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| 6,443,970 B1 | 9/2002 | Schulze et al. |
| D465,281 S | 11/2002 | Lang |
| D466,209 S | 11/2002 | Bon |
| 6,508,816 B2 | 1/2003 | Shadduck |
| 6,626,901 B1 | 9/2003 | Treat et al. |
| 6,663,639 B1 | 12/2003 | Laufer et al. |
| 6,689,131 B2 | 2/2004 | McClurken |
| 6,726,694 B2 | 4/2004 | Blatter et al. |
| 6,743,239 B1 | 6/2004 | Kuehn et al. |
| D493,888 S | 8/2004 | Reschke |
| 6,773,409 B2 | 8/2004 | Truckai et al. |
| 6,773,441 B1 | 8/2004 | Laufer et al. |
| 6,786,905 B2 | 9/2004 | Swanson et al. |
| D496,997 S | 10/2004 | Dycus et al. |
| D499,181 S | 11/2004 | Dycus et al. |
| D502,994 S | 3/2005 | Blake, III |
| 6,860,880 B2 | 3/2005 | Treat et al. |
| 6,908,463 B2 | 6/2005 | Treat et al. |
| 6,932,816 B2 | 8/2005 | Phan |
| D509,297 S | 9/2005 | Wells |
| 7,052,489 B2 | 5/2006 | Griego et al. |
| D525,361 S | 7/2006 | Hushka |
| D531,311 S | 10/2006 | Guerra et al. |
| 7,115,139 B2 | 10/2006 | McClurken et al. |
| D533,274 S | 12/2006 | Visconti et al. |
| D533,942 S | 12/2006 | Kerr et al. |
| D535,027 S | 1/2007 | James et al. |
| 7,160,299 B2 | 1/2007 | Baily |
| 7,169,146 B2 | 1/2007 | Truckai et al. |
| 7,179,255 B2 | 2/2007 | Lettice et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,318,823 B2 | 1/2008 | Sharps et al. |
| D564,662 S | 3/2008 | Moses et al. |
| D567,943 S | 4/2008 | Moses et al. |
| 7,367,976 B2 | 5/2008 | Lawes et al. |
| D575,395 S | 8/2008 | Hushka |
| D575,401 S | 8/2008 | Hixson et al. |
| 7,414,724 B2 | 8/2008 | Eckert et al. |
| D582,038 S | 12/2008 | Swoyer et al. |

(56) References Cited

U.S. PATENT DOCUMENTS

| | | |
|---|---|---|
| 7,588,565 B2 | 9/2009 | Marchitto et al. |
| 7,655,007 B2 | 2/2010 | Baily |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,753,908 B2 | 7/2010 | Swanson |
| D621,503 S | 8/2010 | Otten et al. |
| 7,775,103 B2 | 8/2010 | Veerasamy |
| D627,462 S | 11/2010 | Kingsley |
| D628,289 S | 11/2010 | Romero |
| D628,290 S | 11/2010 | Romero |
| D630,324 S | 1/2011 | Reschke |
| 7,967,839 B2 | 6/2011 | Flock et al. |
| 8,012,166 B2 | 9/2011 | Rizvi |
| D649,249 S | 11/2011 | Guerra |
| D649,643 S | 11/2011 | Allen, IV et al. |
| 8,469,716 B2 | 6/2013 | Fedotov et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,679,098 B2 | 3/2014 | Hart |
| 8,685,009 B2 | 4/2014 | Chernov et al. |
| 8,685,021 B2 | 4/2014 | Chernov et al. |
| 8,685,056 B2 | 4/2014 | Evans et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,434 B2 | 6/2014 | Larson et al. |
| 8,756,785 B2 | 6/2014 | Allen, IV et al. |
| 8,784,418 B2 | 7/2014 | Romero |
| 8,840,639 B2 | 9/2014 | Gerhardt, Jr. et al. |
| 8,845,636 B2 | 9/2014 | Allen, IV et al. |
| 8,852,185 B2 | 10/2014 | Twomey |
| 8,852,228 B2 | 10/2014 | Nau, Jr. |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,898,888 B2 | 12/2014 | Brandt et al. |
| 8,900,232 B2 | 12/2014 | Ourada |
| 8,920,421 B2 | 12/2014 | Rupp |
| 8,932,293 B2 | 1/2015 | Chernov et al. |
| 8,936,614 B2 | 1/2015 | Allen, IV |
| 8,939,572 B2 | 1/2015 | Perez Gellida et al. |
| 8,945,175 B2 | 2/2015 | Twomey |
| 8,961,513 B2 | 2/2015 | Allen, IV et al. |
| 8,961,515 B2 | 2/2015 | Twomey et al. |
| 8,968,283 B2 | 3/2015 | Kharin |
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |
| 8,968,310 B2 | 3/2015 | Twomey et al. |
| 8,968,316 B2 | 3/2015 | Roy et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,484 B2 | 5/2015 | Craig |
| 9,028,492 B2 | 5/2015 | Kerr et al. |
| 9,039,704 B2 | 5/2015 | Joseph |
| 9,039,732 B2 | 5/2015 | Sims et al. |
| 9,060,780 B2 | 6/2015 | Twomey et al. |
| 9,113,882 B2 | 8/2015 | Twomey et al. |
| 9,113,899 B2 | 8/2015 | Garrison et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,113,940 B2 | 8/2015 | Twomey |
| 9,161,807 B2 | 10/2015 | Garrison |
| 9,216,700 B2 | 12/2015 | Gordon |
| 9,259,268 B2 | 2/2016 | Behnke, II et al. |
| 9,265,565 B2 | 2/2016 | Kerr |
| 9,265,568 B2 | 2/2016 | Chernov et al. |
| 9,314,295 B2 | 4/2016 | Garrison |
| 9,333,002 B2 | 5/2016 | Garrison |
| 9,375,282 B2 * | 6/2016 | Nau, Jr. ............... A61B 18/22 |
| 9,381,059 B2 | 7/2016 | Garrison |
| 9,610,121 B2 * | 4/2017 | Nau, Jr. ............... A61B 18/22 |
| 2003/0069571 A1 | 4/2003 | Treat et al. |
| 2003/0127872 A1 * | 7/2003 | Mannhart ............... B25B 5/16 |
| | | 294/106 |
| 2003/0158548 A1 | 8/2003 | Phan et al. |
| 2003/0158549 A1 | 8/2003 | Swanson |
| 2003/0171741 A1 | 9/2003 | Ziebol et al. |
| 2003/0216732 A1 | 11/2003 | Truckai et al. |
| 2003/0236518 A1 | 12/2003 | Marchitto et al. |
| 2004/0073256 A1 | 4/2004 | Marchitto et al. |
| 2004/0210282 A1 | 10/2004 | Flock et al. |
| 2004/0260281 A1 | 12/2004 | Baxter et al. |
| 2005/0033278 A1 | 2/2005 | McClurken et al. |
| 2005/0059934 A1 | 3/2005 | Wenchell et al. |
| 2005/0131390 A1 | 6/2005 | Heinrich et al. |
| 2006/0224154 A1 | 10/2006 | Shadduck et al. |
| 2007/0156140 A1 | 7/2007 | Baily |
| 2007/0167678 A1 | 7/2007 | Moskowitz et al. |
| 2007/0225695 A1 | 9/2007 | Mayer et al. |
| 2008/0046122 A1 | 2/2008 | Manzo et al. |
| 2008/0247594 A1 | 10/2008 | Leclear et al. |
| 2008/0281311 A1 | 11/2008 | Dunning et al. |
| 2008/0319442 A1 | 12/2008 | Unger et al. |
| 2009/0138029 A1 | 5/2009 | Saliman et al. |
| 2009/0145194 A1 | 6/2009 | Clayton et al. |
| 2009/0318912 A1 | 12/2009 | Mayer et al. |
| 2010/0049187 A1 | 2/2010 | Carlton et al. |
| 2010/0063500 A1 | 3/2010 | Muszala |
| 2010/0094271 A1 | 4/2010 | Ward et al. |
| 2010/0100122 A1 | 4/2010 | Hinton |
| 2010/0130971 A1 | 5/2010 | Baily |
| 2010/0228249 A1 | 9/2010 | Mohr et al. |
| 2011/0224485 A1 | 9/2011 | Boulnois et al. |
| 2011/0251605 A1 | 10/2011 | Hoarau et al. |
| 2012/0209263 A1 | 8/2012 | Sharp et al. |
| 2012/0296205 A1 | 11/2012 | Chernov et al. |
| 2012/0296238 A1 | 11/2012 | Chernov et al. |
| 2012/0296323 A1 | 11/2012 | Chernov et al. |
| 2012/0323238 A1 | 12/2012 | Tyrrell et al. |
| 2013/0018364 A1 | 1/2013 | Chernov et al. |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079774 A1 | 3/2013 | Whitney et al. |
| 2013/0085496 A1 | 4/2013 | Unger et al. |
| 2013/0103031 A1 | 4/2013 | Garrison |
| 2013/0197503 A1 | 8/2013 | Orszulak |
| 2017/0367772 A1 * | 12/2017 | Gunn .................. A61B 90/36 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3712328 A1 | 10/1988 |
| DE | 04303882 C2 | 2/1995 |
| DE | 04403252 A1 | 8/1995 |
| DE | 4434938 C1 | 2/1996 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10045375 A1 | 4/2002 |
| DE | 102004026179 A1 | 12/2005 |
| DE | 202007009165 U1 | 8/2007 |
| DE | 202007009317 U1 | 10/2007 |
| DE | 202007016233 U1 | 1/2008 |
| DE | 102008018406 B3 | 7/2009 |

(56) References Cited

FOREIGN PATENT DOCUMENTS

| | | |
|---|---|---|
| EP | 0480293 A1 | 4/1992 |
| EP | 0589555 A1 | 3/1994 |
| EP | 0776739 A2 | 6/1997 |
| EP | 1177771 A1 | 2/2002 |
| EP | 1278007 A1 | 1/2003 |
| EP | 1159926 A2 | 3/2003 |
| EP | 1842500 A2 | 10/2007 |
| EP | 2113218 A2 | 11/2009 |
| EP | 02241280 A2 | 10/2010 |
| JP | 53145385 | 12/1978 |
| JP | 61501068 | 9/1984 |
| JP | 6502328 | 3/1992 |
| JP | 540112 | 2/1993 |
| JP | 6121797 | 5/1994 |
| JP | 6285078 | 10/1994 |
| JP | 6343644 | 12/1994 |
| JP | 6511401 | 12/1994 |
| JP | 7265328 | 10/1995 |
| JP | 856955 | 3/1996 |
| JP | 08098799 A | 4/1996 |
| JP | H08503626 A | 4/1996 |
| JP | 8252263 | 10/1996 |
| JP | 8289895 | 11/1996 |
| JP | 8317934 | 12/1996 |
| JP | 8317936 | 12/1996 |
| JP | 910223 | 1/1997 |
| JP | 9122138 | 5/1997 |
| JP | 1024051 | 1/1998 |
| JP | 10155798 | 6/1998 |
| JP | 1147150 | 2/1999 |
| JP | 11070124 | 3/1999 |
| JP | 11169381 | 6/1999 |
| JP | 11192238 | 7/1999 |
| JP | 11244298 A | 9/1999 |
| JP | 2000102545 A | 4/2000 |
| JP | 2000342599 A | 12/2000 |
| JP | 2000350732 A2 | 12/2000 |
| JP | 2001003400 A | 1/2001 |
| JP | 2001008944 | 1/2001 |
| JP | 2001029356 | 2/2001 |
| JP | 2001128990 A | 5/2001 |
| JP | 2001190564 A | 7/2001 |
| JP | 2002528166 A | 9/2002 |
| JP | 2003245285 A | 9/2003 |
| JP | 2004517668 A | 6/2004 |
| JP | 2004528869 A | 9/2004 |
| JP | 2011125195 A | 6/2011 |
| JP | 6030945 B2 | 11/2016 |
| SU | 401367 A1 | 10/1973 |
| WO | 8503781 A1 | 8/1985 |
| WO | 9408526 A1 | 4/1994 |
| WO | 9814124 A1 | 4/1998 |
| WO | 0036986 A1 | 6/2000 |
| WO | 0059392 A1 | 10/2000 |
| WO | 0101847 A1 | 1/2001 |
| WO | 0115614 A1 | 3/2001 |
| WO | 0154604 A1 | 8/2001 |
| WO | 03090630 A2 | 11/2003 |
| WO | 2005110264 A2 | 4/2006 |
| WO | 2007032900 A2 | 3/2007 |
| WO | 20080112147 A1 | 9/2008 |
| WO | 20090005850 A1 | 1/2009 |
| WO | 2010060097 A2 | 5/2010 |
| WO | 2010104753 A1 | 9/2010 |
| WO | 2012158777 A1 | 11/2012 |
| WO | 2012158788 A1 | 11/2012 |

OTHER PUBLICATIONS

Int'l Search Report EP 07 001480.8 dated Apr. 19, 2007.
Japanese Office Action dated Nov. 7, 2017 issued in corresponding Japanese Application No. 2015-503220 (Summary only).
European Examination Report dated Feb. 7, 2019 issued in corresponding EP Appln. No. 13767281.2.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy"; FIGO 2000, Washington, D.C.
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005; LNCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Japanese Office Action for application No. 2015-503220 dated Sep. 29, 2016.
Chinese Office Action for Application No. 2013.80016698.X dated May 26, 2017.

(56) References Cited

OTHER PUBLICATIONS

Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 10672.9 dated Oct. 16, 2007.
Int'l Search Report EP 07 13779.9 dated Oct. 26, 2007.
Int'l Search Report EP 07 14016 dated Jan. 28, 2008.
Int'l Search Report EP 07 15191.5 dated Jan. 23, 2008.
Int'l Search Report EP 07 15601.3 dated Jan. 4, 2008.
Int'l Search Report EP 07 16911 dated May 28, 2010.
Int'l Search Report Ep 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 16539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 10521.4 dated Dec. 16, 2009.
Int'l Search Report EP 09 11745.8 dated Jan. 5, 2010.
Int'l Search Report EP 09 12629.3 dated Dec. 8, 2009.
Int'l Search Report EP 09 12687.1 dated Dec. 23, 2009.
Int'l Search Report EP 09 12688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 11750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 167655.9 dated Aug. 31, 2011.
Japanese Office Action for appliction No. 2015-503220 dated Mar. 28, 2017.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
EP Search Report for Application No. 13767281.2 dated Oct. 14, 2015.
Int'l Search Report EP 10 168705.1 dated Oct. 4, 2010.
Int'l Search Report EP 10.169647.4 dated Oct. 29, 2010.
International Search Report from corresponding PCT Application No. PCT/US2013/028520 dated Jun. 26, 2013.
Office Action issued in U.S. Appl. No. 11/568,553, dated Nov. 30, 2009.
The Written Opinion from the International Searching Authority from Appl. No. PCT/US2008/052460 dated Jan. 5, 2010.
U.S. Appl. No. 08/926,869, filed Sep. 10, 1997, James G. Chandler, abandoned.
U.S. Appl. No. 09/177,950, filed Oct. 23, 1998, Randel A. Frazier, abandoned.
U.S. Appl. No. 09/387,883, filed Sep. 1, 1999, Dale F. Schmaltz, abandoned.
U.S. Appl. No. 09/591,328, filed Jun. 9, 2000 Thomas P. Ryan, abandoned.
U.S. Appl. No. 12/336,970, filed Dec. 17, 2008, Paul R. Sremeich, abandoned.
U.S. Appl. No. 12/947,352, filed Nov. 16, 2010, Jason L. Craig, abandoned.
U.S. Appl. No. 12/981,787, filed Dec. 30, 2010, John R. Twomey, abandoned.
U.S. Appl. No. 13/050,182, filed Mar. 17, 2011, Glenn A. Homer., abandoned.
U.S. Appl. No. 13/085,144, filed Apr. 12, 2011, Keir Hart, abandoned.
U.S. Appl. No. 13/166,477, filed Jun. 22, 2011, Daniel A. Joseph, abandoned.
U.S. Appl. No. 13/185,593, filed Jul. 19, 2011, James D. Allen, IV, abandoned.
Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of the Gyms PlasmaKinetic Sealer and the Valleylab LigaSure Device in the Hemostasis of Small,

(56) References Cited

OTHER PUBLICATIONS

Medium, and Large-Sized Arteries" Carolinas Laparoscopic and Advanced Surgery Program, Carolinas Medical Center, Charlotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview", Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectomy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties At VHF Through Microwave Frequencies", IEEE Transactions on Microwave Theory and Techniques vol. MTT-28, No. 4, Apr. 1980 pp. 414-427.
Carus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer"; Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA , Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Canadian Office Action dated Dec. 27, 2018 issued in corresponding CA Appln. No. 2,866,686.
European Examination Report dated May 6, 2020 issued in corresponding EP Appln. No. 13767281.2.

\* cited by examiner

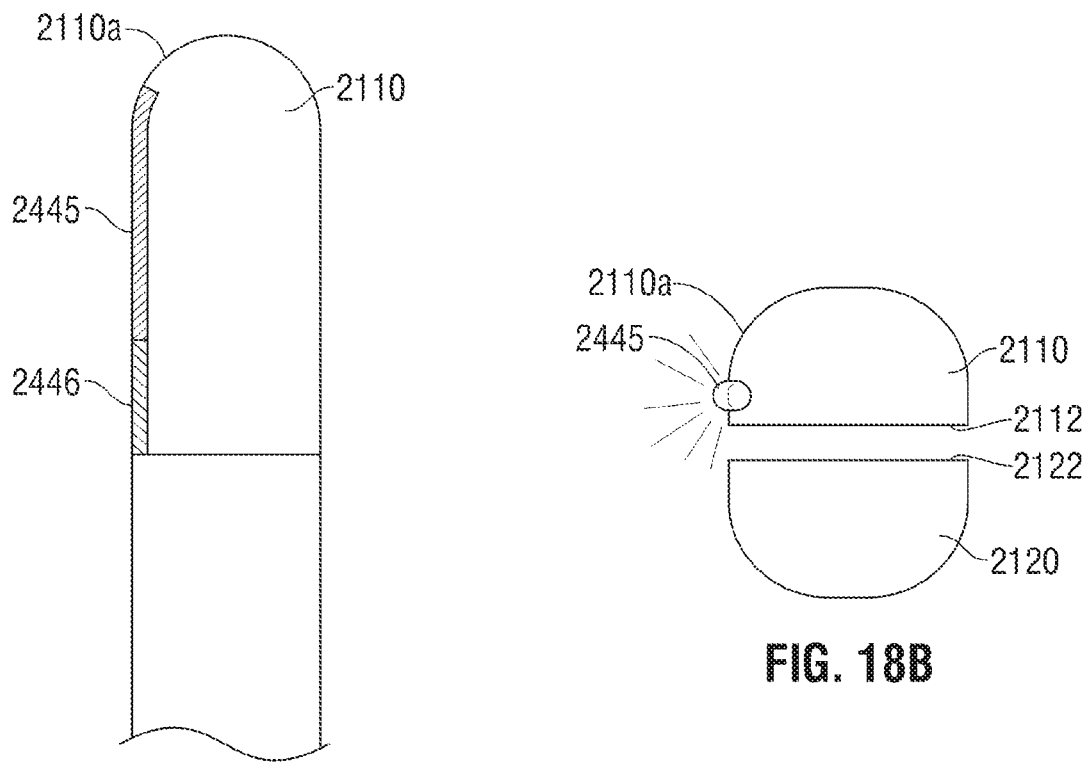
FIG. 18A
FIG. 18B
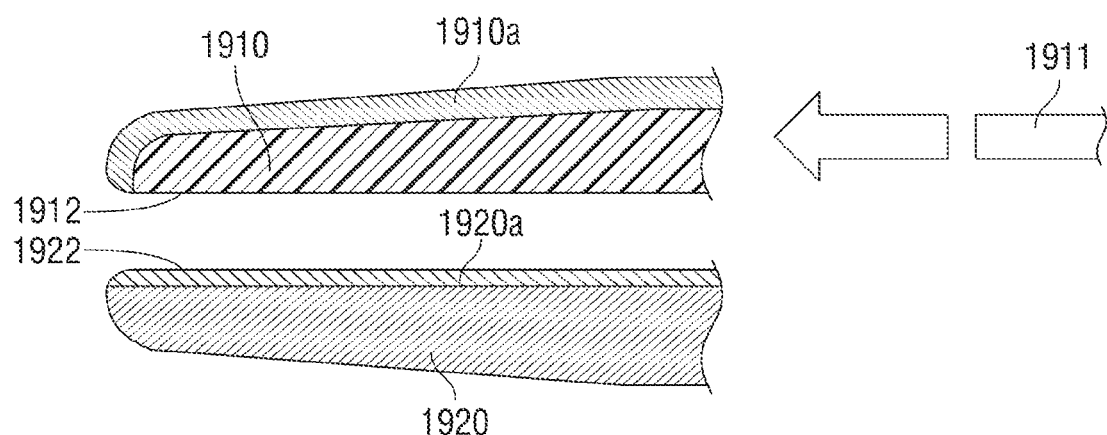
FIG. 19

LIGHT ENERGY SEALING, CUTTING, AND SENSING SURGICAL DEVICE

CROSS-REFERENCE TO RELATED APPLICATION

This application is a continuation of U.S. patent application Ser. No. 15/912,899, filed on Mar. 6, 2018, which is a continuation of U.S. patent application Ser. No. 15/458,634, filed on Mar. 14, 2017, now U.S. Pat. No. 9,925,008, which is a continuation of U.S. patent application Ser. No. 15/191,697, filed on Jun. 24, 2016, now U.S. Pat. No. 9,610,121, which is a divisional application of U.S. patent application Ser. No. 13/430,325, filed on Mar. 26, 2012, now U.S. Pat. No. 9,375,282. The entire disclosures of each of the foregoing applications are hereby incorporated by reference herein.

BACKGROUND

Technical Field

The present disclosure relates to surgical forceps having components to treat and/or monitor tissue being treated. More particularly, the present disclosure relates to open or endoscopic surgical forceps that utilize light energy to treat (e.g, seal, cut, etc.) and/or to sense tissue properties.

Description of Related Art

In many surgical procedures, body vessels, e.g., blood vessels, ducts, adhesions, fallopian tubes, or the like are sealed to defunctionalize or close the vessels. Traditionally, staples, clips or sutures have been used to close a body vessel. However, these traditional procedures often leave foreign body material inside a patient. In an effort to reduce foreign body material left within the patient and to more effectively seal the body vessel, energy techniques that seal by heating tissue have been employed.

Endoscopic or open forceps are particularly useful for sealing since forceps utilize mechanical action to constrict, grasp, dissect and/or clamp tissue. Current vessel sealing procedures utilize radio frequency treatment to heat and desiccate tissue causing closure and sealing of vessels or tissue. Other treatment methods are known in the art, however, very few surgical instruments have the capability to treat and monitor tissue treatment without the use of additional surgical instruments.

SUMMARY

In accordance with one aspect of the present disclosure, a medical instrument is provided. The instrument includes a housing and an end effector assembly operably connected to the housing. The end effector assembly includes first and second jaw members each having a tissue contacting surface, at least one of the first and second jaw members movable between a first, spaced-apart position and a second proximate position. In the second position, the jaw members cooperate to define a cavity that is configured to receive tissue between the jaw members. One or more light-transmissive element is coupled to at least one of the first and second jaw members. The light-transmissive element(s) is adapted to connect to a light energy source and to transmit the light energy to tissue grasped between the first and second jaw members to treat the tissue.

The present disclosure also provides for a system for treating tissue. The system includes a medical instrument including a housing and an end effector assembly operably connected to the housing. The end effector assembly includes first and second jaw members each having a tissue contacting surface, at least one of the first and second jaw members movable between a first, spaced-apart position and a second proximate position. In the second position, the jaw members cooperate to define a cavity that is configured to receive tissue between the jaw members. One or more light-transmissive element is coupled to at least one of the first and second jaw members. The light-transmissive element(s) is adapted to connect to a light energy source and to transmit the light energy to tissue grasped between the first and second jaw members to treat the tissue and one or more light-detecting element(s) configured to measure at least one property of the light energy passing through the tissue. The system also includes a controller coupled to the light-detecting element(s) and the light energy source, the controller configured to control the light energy source based on the at least one measured property of the light energy passing through the tissue.

A method for treating tissue is also contemplated by the present disclosure. The method includes grasping tissue between first and second jaw members, at least one of the first and second jaw members movable between a first, spaced-apart position and a second proximate position, wherein in the second position, the jaw members cooperate to define a cavity that is configured to receive tissue between the jaw members; applying light energy to the tissue grasped between the first and second jaw members; measuring at least one property of the light energy applied to the tissue; and controlling the light energy based on the at least one measured property of the light energy.

Aspects of the presently-disclosed surgical instrument are described in detail with reference to the drawings wherein like reference numerals identify similar or identical elements. As used herein, the term "distal" refers to that portion that is further from an operator while the term "proximal" refers to that portion that is closer to an operator. As used herein, the term "treat" refers to performing a surgical treatment to tissue including, but not limited to heating, sealing, cutting, sensing and/or monitoring. As used herein, the term "light energy source" refers broadly to include all types of devices that produce light for medical use (e.g., tissue treatment). These devices include lasers, light emitting diodes (LEDs), lamps, and other devices that produce light anywhere along an appropriate part of the electromagnetic spectrum (e.g., from infrared to ultraviolet). It is also to be understood that the light sources disposed herein may be used interchangeably, such that, if an LED light source is disclosed, a laser light source may also be used, unless stated otherwise.

The present disclosure provides systems and method for treating tissue by delivering light thereto. This may be accomplished by placing a light source in intimate contact with the target tissue. In some embodiments, it may be accomplished by connecting a light source to the target tissue with an optical system designed to transmit the light from a light source to the tissue. Either system may include elements that shape the distribution of optical energy as it impinges on and interacts with the target tissue. As herein, the term "light-emitting elements" denotes any device from which light exits prior to interacting with the target tissue including, but not limited light sources; the end of a light transmission system terminating at the target tissue; refracting, diffracting, transmitting or reflecting optical elements such as lenses, diffraction gratings, windows and mirrors, and combinations thereof.

Laser light sources may produce light having a wavelength from about 200 nm to about 15,000 nm and include but are not limited to ruby lasers, tunable titanium-sapphire lasers, copper vapor lasers, carbon dioxide lasers, alexandrite lasers, argon lasers such as argon fluoride (ArF) excimer lasers, argon-dye lasers, potassium titanyl phosphate (KTP) lasers, krypton lasers such as krypton fluoride (KrF) excimer lasers, neodymium:yttrium-aluminum-garnet (Nd:YAG) lasers, holmium:yttrium-aluminum-garnet (Ho:YAG) lasers, erbium:yttrium-aluminum-garnet (Er:YAG) lasers, diode lasers, fiber lasers, xenon chloride (XeCl) excimer lasers, tunable thalium lasers, and combinations thereof. Additional light source types also include fiber optic light sources and deuterium light sources.

In some aspects of the present disclosure, light may be generated at multiple wavelengths. For example, Nd:YAG and KTP lasers may be part of a single light source. Nd:YAG with a greater optical depth in tissue may be used for sealing and KTP with a shorter optical depth may be used for sealing smaller vessels, thinner tissue, or for cutting. As used herein, the term "receiving module" refers to a component or apparatus having the capability of receiving and/or sensing a signal (e.g., light energy and heat energy) and analyzing the received signal to generate a control and/or output signal (e.g., instruction and/or indication to a user). It should be noted that the receiving module may also transmit the received signal to some other suitable component for analysis thereof (e.g., a processor and/or generator).

As described in more detail below with reference to the accompanying figures, the present disclosure generally relates to surgical light energy devices that include an end effector assembly that can fuse (e.g., seal) and/or separate (e.g., cut) tissue. The present disclosure also provides one or more devices that sense and/or monitor tissue properties at various stages of treatment to determine when the treatment is complete, efficacy of a tissue seal and/or to measure jaw pressure (e.g., a potential requirement for a quality seal). Optical sensing provides better indication of seal quality than current methods, such as, electrical impedance measurements. Additionally, tissue separation may be accomplished with the same light energy device used for tissue sealing eliminating the need for a separate mechanical blade that is traditionally used for tissue separation in jaw members. The present disclosure also provides one or more methods for providing feedback to the user, generator and/or control algorithm with regard to temperature at or proximate a surgical site, jaw closure pressure, jaw positioning, and other various feedback information.

Any of the following aspects and components thereof of the present disclosure may be interchangeably combined with one or more other embodiments. For example, coating on the surfaces of the jaw members may be included in each of the embodiments and various disclosed monitoring and control processes may be utilized with various jaw member embodiments.

BRIEF DESCRIPTION OF THE DRAWINGS

Various embodiments of the subject instrument are described herein with reference to the drawings wherein:

FIG. 18A is a top view of a jaw member including a light dissection element disposed on an outer periphery thereof according to an embodiment of the present disclosure;

FIG. 18B is a front cross-sectional of a jaw member including a light dissection element disposed on an outer periphery thereof according to an embodiment of the present disclosure;

FIG. 19 is a side, cross-sectional view of an end effector assembly according to an embodiment of the present disclosure;

DETAILED DESCRIPTION

Figure 1A:
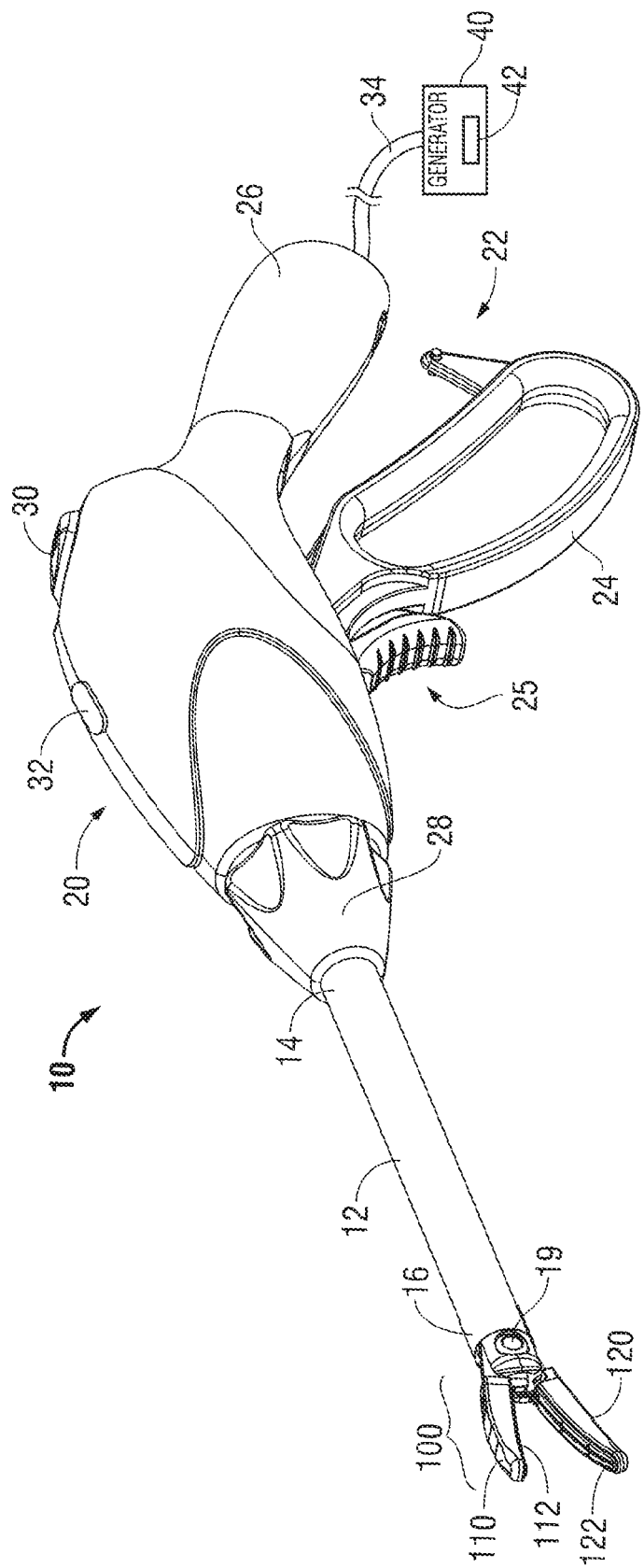
FIG. 1A is a perspective view of an endoscopic forceps having an end effector assembly attached to a distal end of the forceps according to an embodiment of the present disclosure.
Figure 1B:
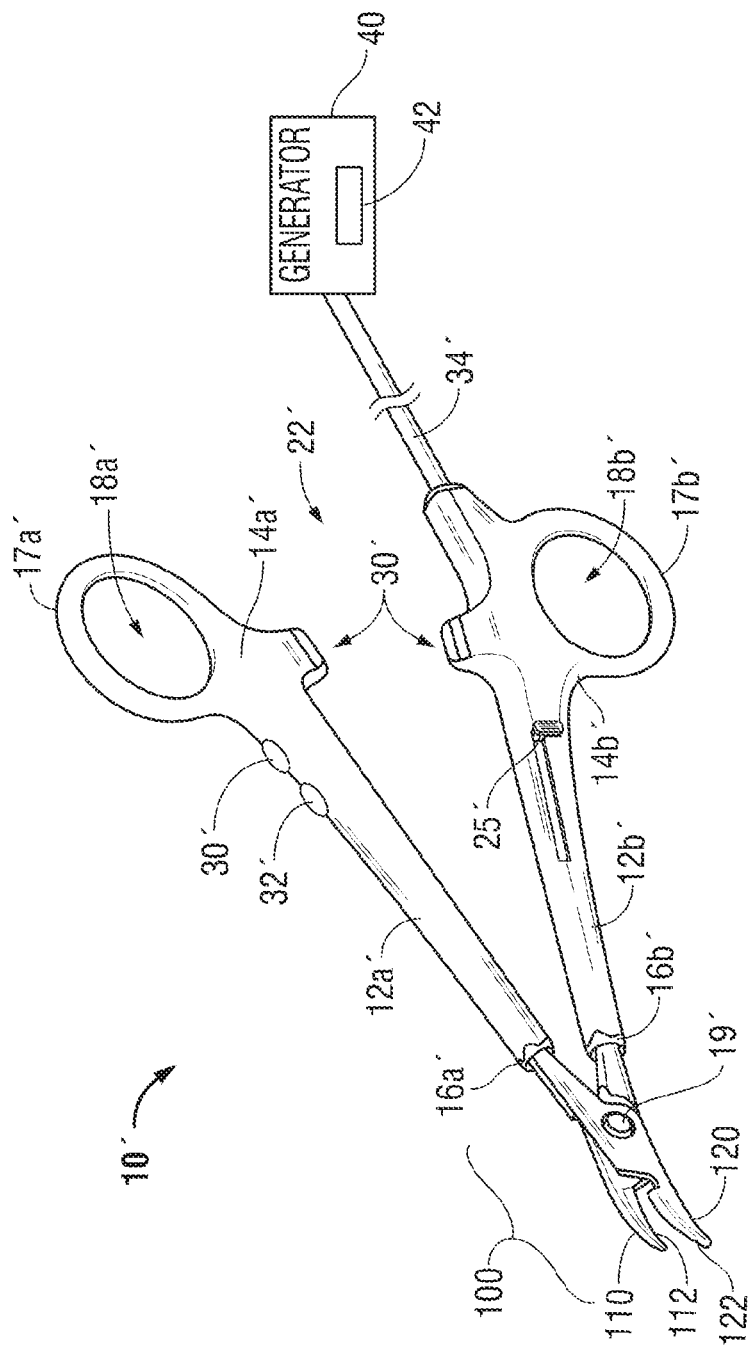
FIG. 1B is a perspective view of an open forceps having a handle assembly and an end effector assembly attached to a distal end of the handle assembly according to another embodiment the present disclosure.

Referring now to FIGS. 1A and 1B, an endoscopic surgery forceps 10 and an open forceps 10' are shown, respectively. For the purposes herein, either an endoscopic instrument or an open surgery instrument may be utilized with any of the embodiments of end effector assemblies described herein. It should be noted that different electrical, optical and mechanical connections and other considerations may apply to each particular type of instrument. However, the novel aspects, with respect to the end effector assembly and the operating characteristics thereof, remain generally consistent with respect to both the endoscopic or open surgery designs. It also should be noted that any of the embodiments described below may be configured to also include traditional vessel sealing capabilities.

The present disclosure provides for an apparatus, system and method for sealing tissue using light energy. Light (e.g., from about 200 nm to about 11,000 nm) is used to heat the tissue due to absorption of light. Absorption, transmittance, and scattering of light energy depends on the tissue, the state of the tissue (e.g., hydration, disease state, treatment stage, etc.), and the wavelength of the light. The present disclosure utilizes these factors to control the distribution of the energy within the tissue based on an appropriate choice of the wavelength. More specifically, wavelengths that are strongly absorbed by the tissue deposit energy closer to the surface of the tissue while wavelengths that are weakly absorbed by the tissue are used to deposit a larger fraction of the incident energy deeper in the tissue. In particular, since tissue is relatively transparent to light at certain infrared wavelengths, light energy at infrared frequencies may be used for deeper energy deposition.

In FIG. 1A, forceps 10 is coupled to a light energy source (e.g., a generator 40) for generating light energy adapted to treat tissue. Generator 40 is configured to output various types of energy, such as light energy having a wavelength from about 200 nm to about 11,000 nm. Forceps 10 is coupled to the generator 40 via a cable 34 that is adapted to transmit light energy and control signals therebetween. Various embodiments of the forceps 10 utilizing the aforementioned light energy are discussed in more detail below.

Forceps 10 is configured to support an end effector assembly (e.g., end effector assembly 100). Forceps 10 includes a housing 20, a handle assembly 22, a trigger assembly 25, and a rotating assembly 28 that enable forceps 10 and end effector assembly 100 to mutually cooperate to grasp, seal, divide and/or sense tissue. Forceps 10 generally includes housing 20 and handle assembly 22 that includes moveable handle 24 and fixed handle 26 that is integral with housing 20. Handle 24 is moveable relative to fixed handle 26 to actuate end effector assembly 100 via a drive assembly (not shown) to grasp tissue.

In some embodiments, trigger assembly 25 may be configured to actuate a cutting function of the forceps 10 or another component, as described in further detail below. Forceps 10 also includes a shaft 12 having a distal portion 16 that mechanically engages end effector assembly 100 and a proximal portion 14 that mechanically engages housing 20 proximate rotating assembly 28. Rotating assembly 28 is mechanically associated with shaft 12 such that rotational movement of rotating assembly 28 imparts similar rotational movement to shaft 12 that, in turn, rotates end effector assembly 100.

End effector assembly 100 includes two jaw members 110 and 120. One or both jaw members 110 and 120 are pivotable about a pin 19 and one or both are movable from a first position wherein jaw members 110 and 120 are spaced relative to another, to a second position wherein jaw members 110 and 120 are closed and cooperate to grasp tissue therebetween.

Figure 2A:
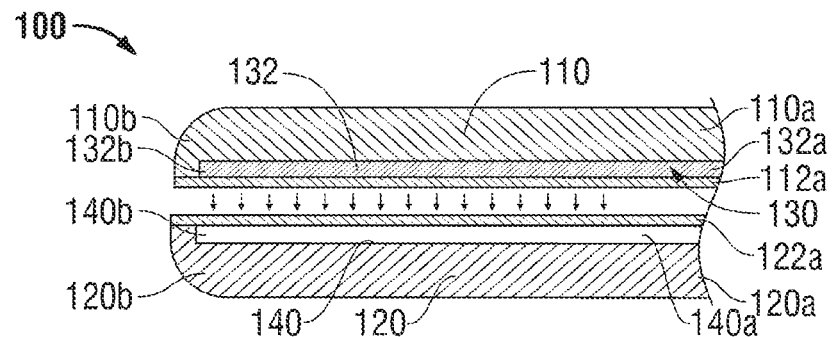
FIG. 2A is a side, cross-sectional view of an end effector assembly according to an embodiment of the present disclosure.
Figure 2B:
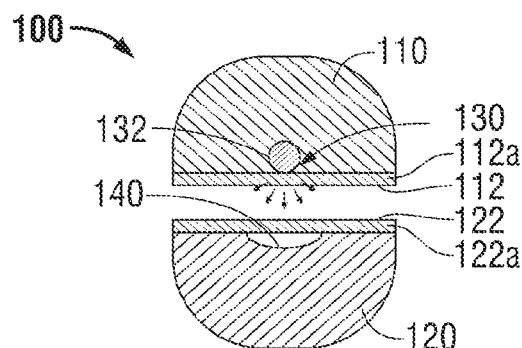
FIG. 2B is a front, cross-sectional view of the end effector assembly of FIG. 2A.

Each jaw member 110 and 120 includes a tissue contacting surface 112 and 122, respectively, disposed on an inner-facing surface thereof (see FIG. 2B). Tissue contacting surfaces 112 and 122 cooperate to grasp and seal tissue held therebetween upon application of energy from generator 40. Tissue contacting surfaces 112 and 122 are connected to the generator 40 such that light energy can be transmitted to and/or through the tissue held therebetween.

First and second switch assemblies 30 and 32 are configured to selectively provide light energy to end effector assembly 100. More particularly, the first switch assembly 30 may be configured to perform a first type of surgical procedure (e.g., seal, cut, and/or sense) and a second switch assembly 32 may be configured to perform a second type of surgical procedure (e.g., seal, cut, and/or sense). It should be noted that the presently disclosed embodiments may include any number of suitable switch assemblies and are not limited to only switch assemblies 30 and 32. It should further be noted that the presently disclosed embodiments may be configured to perform any suitable surgical procedure and are not limited to only sealing, cutting and sensing.

Handle assembly 20 further includes one or more-light transmissive elements, such as a cable 34 that connects the forceps 10 to generator 40. The cable 34 may include a plurality of optical fibers to transmit light energy through various paths and ultimately to end effector assembly 100 and one or more optical fibers.

First and second switch assemblies 30 and 32 may also cooperate with a controller 42 (e.g., logic circuit, computer, processor, field programmable gate array, and the like) that automatically triggers one of the switches to change between a first mode (e.g., sealing mode) and a second mode (e.g., cutting mode) upon the detection of one or more parameters or thresholds. In some embodiments, the controller 42 is also configured to receive various sensor feedback and to control the generator 40 based on the sensor feedback. Embodiments of the present disclosure allow the jaw members 110 and 120 to seal and/or cut tissue using light energy. In some embodiments, the controller 42 may include a feedback loop that indicates when a tissue seal is complete based upon one or more of the following parameters: tissue temperature, optical sensing, change in impedance of the tissue over time and/or changes in the optical or electrical power or current applied to the tissue over time, rate of change of these properties and combinations thereof. An audible or visual feedback monitor may be employed to convey information to the surgeon regarding the overall seal quality or the completion of an effective tissue seal.

Referring now to FIG. 1B, an open forceps 10' is depicted and includes end effector assembly 100 (similar to forceps 10) that is attached to a handle assembly 22' that includes a pair of elongated shaft portions 12a' and 12b'. Each elongated shaft portion, 12a' and 12b', respectively, has a proximal end 14a' and 14b', respectively, and a distal end 16a' and 16b', respectively. The end effector assembly 100 includes jaw members 110 and 120 coupled to distal ends 16a' and 16b' of shafts 12a' and 12b', respectively. The jaw members 110 and 120 are connected about pivot pin 19' that allows jaw members 110 and 120 to pivot relative to one another from the first to second positions for treating tissue (as described above). Tissue contacting surfaces 112 and 122 are connected to opposing jaw members 110 and 120.

Each shaft 12a' and 12b' includes a handle 17a' and 17b', respectively, disposed at the proximal end 14a' and 14b' thereof. Handles 17a' and 17b' facilitate movement of the shafts 12a' and 12b' relative to one another which, in turn, pivot the jaw members 110 and 120 from the open position wherein the jaw members 110 and 120 are disposed in spaced relation relative to one another to the clamping or closed position wherein the jaw members 110 and 120 cooperate to grasp tissue therebetween.

In some embodiments, one or both of the shafts, e.g., shaft 12a', includes a first switch assembly 30' and a second switch assembly 32'. First and second switch assemblies 30' and 32' may be configured to selectively provide energy to the end effector assembly 100. More particularly, the first switch assembly 30' may be configured to perform a first type of surgical procedure (e.g., seal, cut, or sense) and second switch assembly 32' may be configured to perform a second type of surgical procedure (e.g., seal, cut, or sense). In some embodiments, one or both shafts, e.g., 12b', may include a trigger assembly 25' for actuation of an additional laser fiber, e.g., laser fiber 230a and/or 230b (see FIG. 3).

With continued reference to FIG. 1B, forceps 10' is depicted having a cable 34' that connects the forceps 10' to generator 40. In a similar fashion to forceps 10, cable 34' is internally divided within the shaft 12b' to transmit light energy through various transmission paths to the components of end effector assembly 100.

Figure 1C:
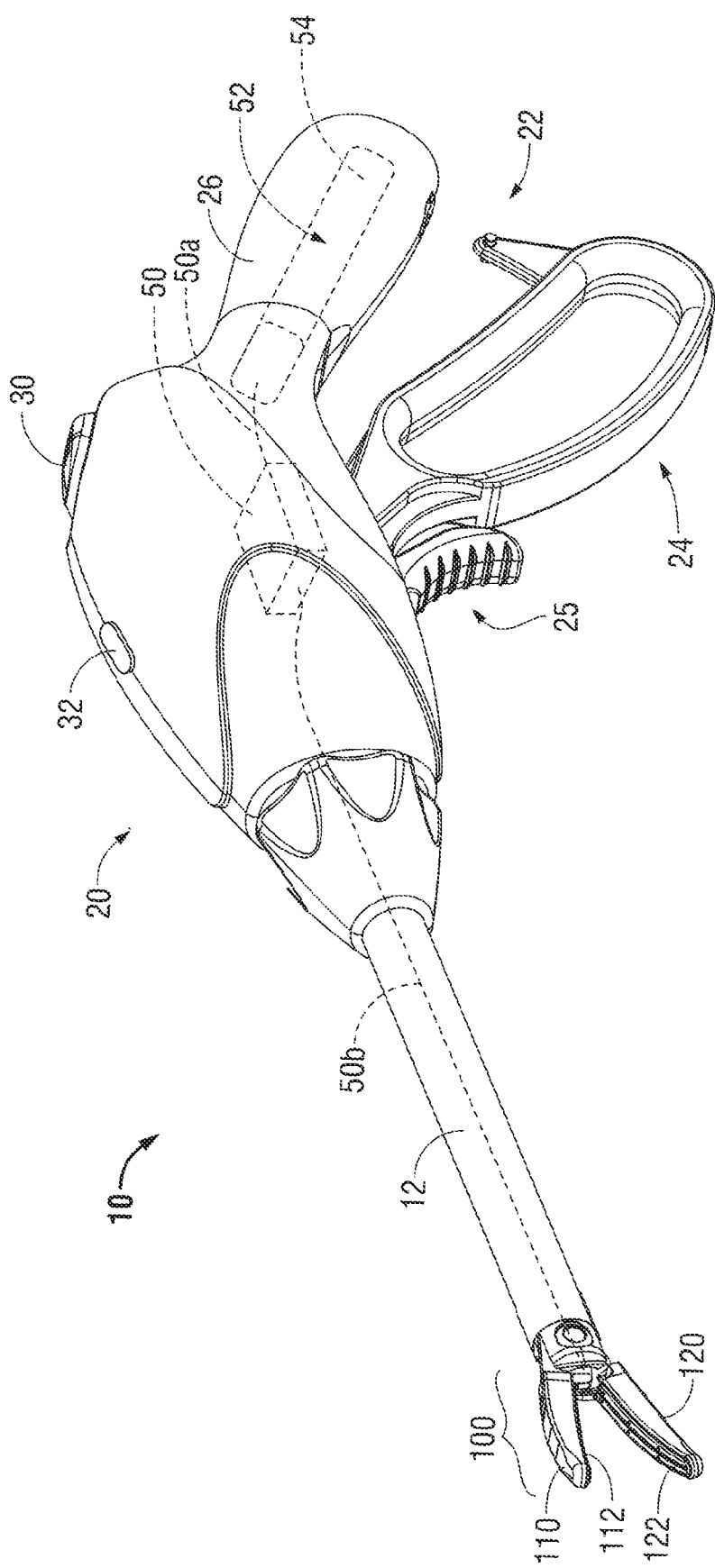
FIG. 1C is a perspective view of a battery-powered endoscopic forceps having an end effector assembly attached to a distal end of the forceps according to another embodiment of the present disclosure.

Referring now to FIG. 1C, forceps 10 is shown having a portable configuration and includes an internal energy source 50 for generating light energy that is operably coupled to a battery compartment 52 via one or more wires 50a. In some embodiments, one or more battery operated laser diodes or fiber lasers may also be used to provide a portable light energy source. Internal energy source 50 may be configured to provide light energy to the end effector assembly 100 and optical elements via one or more laser fibers 50b or any other suitable transmission medium. Battery compartment 52 may be configured to receive one or more batteries 54 for providing suitable energy to internal energy source 50. In some embodiments, the controller 42 may also be disposed within the forceps 10 (e.g., housing).

Battery compartment 52 may be defined within any suitable portion of housing 20 of forceps 10, such as the fixed handle 26, as shown in FIG. 1C. Suitable batteries may include, but are not limited to, a nickel-cadmium, lithium-ion, or any other suitable type. The location of internal energy source 50 provides an operator increased maneuverability and convenience when performing a surgical treatment with forceps 10.

FIGS. 2A and 2B illustrate an end effector assembly 100 according to an embodiment of the present disclosure, which is configured for use with either instrument 10 or instrument 10', discussed above or any other suitable surgical instrument. However, for purposes of simplicity and consistency, end effector 100 will be described hereinbelow with reference to instrument 10.

The end effector assembly 100 includes jaw members 110 and 120 having proximal ends 110a, 120a and distal ends 110b, 120b that each define a groove or channel 130 and 140, respectively, within the jaw members 110 and 120. Jaw member 110 includes a light diffusing element 132 that is disposed on or along tissue contacting surface 112. The light diffusing element 132 may be made from any suitable light diffusing material, such as frosted sapphire crystal. The light diffusing element 132 is disposed within channel 130. Tissue contacting surfaces 112 and 122 may include a reflective surface disposed thereon. In some embodiments, the surface includes, but is not limited to polished metal, coating or any other material that is adapted to reflect light.

In other embodiments, tissue contacting surfaces 112 and 122 may also include a coating or cover 112a and 122a. In some embodiments, the coatings 112a and 122a may be formed from a light absorbing material (e.g., a light absorbent coating), a transparent material, a scattering material, or a reflective material. In some embodiments, the coating 112a may be formed from one material (e.g., transparent) while the coating 122a may be formed from a different material (e.g., absorbent or reflective). In further embodiments, the coatings 112a and 122a may both be formed from the same material, such as a reflective material. Providing both tissue contacting surfaces 112 and 122 with reflective surfaces increases absorption of the light being supplied to the tissue since the light passes multiple times therethrough, thus lowering the treatment time.

In further embodiments, the coatings 112a and 122a may include a gel or another biocompatible film disposed thereon. The gel or the film may include a dye of a specific color designed to absorb light energy at a specific wavelength. In some embodiments, the gel may be applied to the tissue prior to treatment.

In another embodiment, the coatings 112a and 122a are absorbent coatings formed from a thermochromic material configured to increase absorption properties as temperature increases. As used herein, the term "thermochromic" refers to any material that changes color in response to a change in temperature. As the temperature of the jaw members 110 and 120 increases during application of energy, the absorbent coatings 112*a* and 122*a* become progressively more absorbing and provide more heat to the tissue.

The light diffusing element 132 is coupled to generator 40 via cable 34, which includes one or more a light transporting or light generating fibers therewithin. The generator 40 is adapted to generate a light of a desired wavelength from about 200 nm to about 11,000 nm and transmit the light energy along cable 34 to the forceps 10, 10' and, more specifically, to the light diffusing element 132.

Light diffusing element 132 may have a substantially cylindrical or conical shape and may be formed from a suitable light conducting material (e.g., sapphire crystal, crystal glass, plastic fiber, and the like). More specifically, the light diffusing element 132 may be manufactured from any suitable laser or light conducting medium to obtain desired diffusion properties.

Groove 140 may be configured to fit around or about light diffusing element 132 when the jaw members 110 and 120 are disposed in a closed position. Groove 140 may also have a reflective surface such that light emitted from light diffusing element 132 may pass through tissue and subsequently be reflected back into tissue to form a desired illumination pattern. In some embodiments, groove 140 may have light absorbing properties and/or include a material having light absorbing properties (e.g., a light absorbent coating). In this manner, when light is absorbed, groove 140 and/or the absorbent material may heat to a suitable temperature to operably treat tissue held between jaw members 110 and 120.

During operation, once tissue is grasped between the tissue contacting surfaces 112 and 122, laser light is transmitted from the generator 40 to the light diffusing element 132, which then emits light energy into the tissue. Since the tissue contacting surfaces 112 and 122 are adapted to reflect light, the light energy emitted by the light diffusing element 132 is concentrated in the volume between the jaw members 110 and 120 which in turn, heats up the tissue grasped therebetween without compromising the surrounding tissue. After a preset duration or upon a signal from one or more sensors (described in further detail below), the energy is terminated indicating that the tissue treatment (e.g., seal or cutting) is complete.

Figure 3:
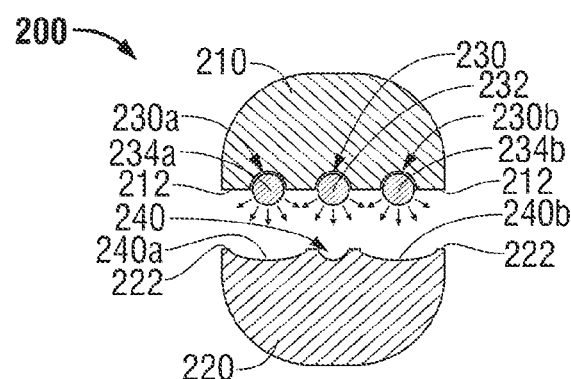
FIG. 3 is a front, cross-sectional view of an end effector assembly according to an embodiment of the present disclosure.

Referring now to FIG. 3, another embodiment of the presently disclosed end effector assembly is shown as end effector assembly 200. End effector assembly 200 includes jaw members 210 and 220 having tissue contacting surfaces 212 and 222. Similar to the above discussed jaw members 110 and 120, jaw members 210 and 220 cooperate to grasp tissue therebetween. Each jaw member 210 and 220 define channels or grooves disposed therealong. More specifically, jaw member 210 includes grooves 230, 230*a*, and 230*b*; and jaw member 220 includes grooves 240, 240*a*, and 240*b*. In some embodiments, jaw member 210 includes a plurality of laser light fibers (e.g., 232, 234*a*, and 234*b*) that span along the length of the jaw member 210 and within respective grooves 230, 230*a*, and 230*b*. The laser fibers are configured to emit a laser light between and along the length of jaw members 210 and 220.

Jaw member 210 includes a centrally-positioned laser fiber 232 that is disposed within channel 230. Alongside of channel 230, jaw member 210 also defines channel or grooves 230*a* and 230*b* that are laterally positioned from channel 230 and include peripheral laser fibers 234*a* and 234*b*. The laser fibers 234*a* and 234*b* may be configured for sealing tissue, based on the type of light energy supplied thereto, pressure applied to the jaw members 210 and 220, as well the reflective or absorbing properties of the grooves disposed about the fibers as described in more detail below. In some embodiments, the tissue contacting surfaces 212 and 222 may include a transparent coating or cover disposed on the surface thereof, similar to the tissue contacting surfaces 112 and 122 of FIGS. 2A and 2B. The laser fiber 232 may be configured to cut tissue after an effective seal has been achieved by laser sealing fibers 234*a* and 234*b*. In some embodiments, cutting may be performed independent of the sealing. In addition, a reflective groove 240 may be disposed on the jaw member 220 such that when laser light is emitted from laser fiber 232, the laser light is reflected from reflective groove 240 back through tissue forming a desired illumination pattern. Additionally or alternatively, laser fibers 234*a* and 234*b* may also have respective reflective or absorbing grooves 240*a* and 240*b* within opposing jaw member 220, as described above.

It should be noted that any number of laser fibers may be used in any of the embodiments discussed in the present disclosure to achieve tissue sealing or cutting based on the light energy transmitted through the laser fibers. Similarly, any number of laser cutting fibers (e.g., laser cutting fiber 232) may be used in any of the embodiments discussed in the present disclosure. In some embodiments, a single laser fiber may also be configured to include sealing and cutting capabilities in any of the embodiments of the present disclosure. It should be noted that any one of the laser fibers may be configured to transmit energy at different wavelengths depending on the surgical treatment (e.g., sealing, cutting and/or sensing). In other embodiments, a particular laser or light fiber may be configured to perform a particular surgical treatment (e.g., sealing, cutting and/or sensing). One or more sensors may be employed or a feedback circuit may be integrated with respect to end effector 200 to signal the user after an effective seal and/or effective separation. An automated seal and cut algorithm may also be employed for this purpose that uses a single activation of a switch, e.g., switch 32, to initiate the process.

Figure 4A:
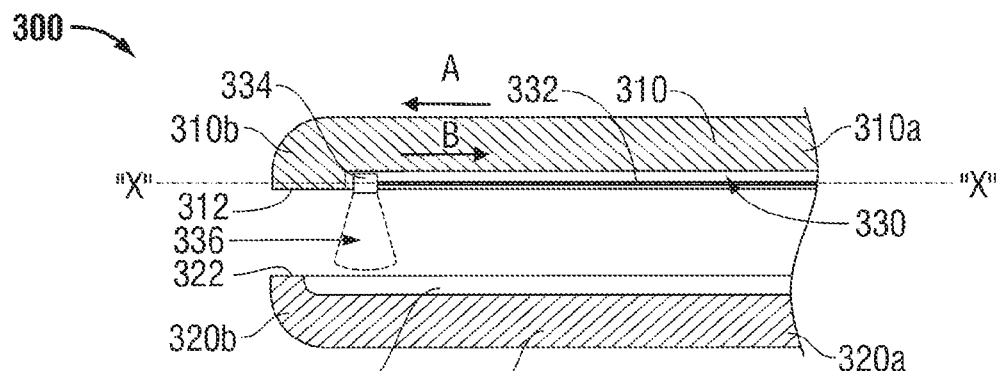
FIG. 4A is a side, cross-sectional view of an end effector assembly according to an embodiment of the present disclosure.
Figure 4B:
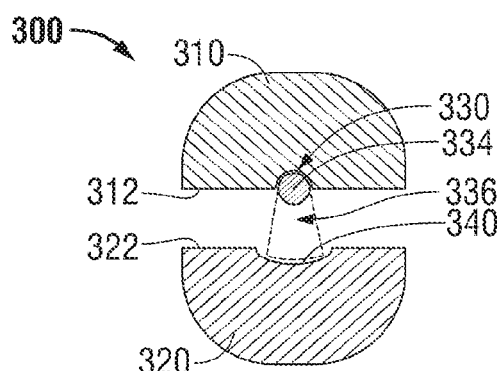
FIG. 4B is a front, cross-sectional view of the end effector assembly of FIG. 4A.
Figure 4C:
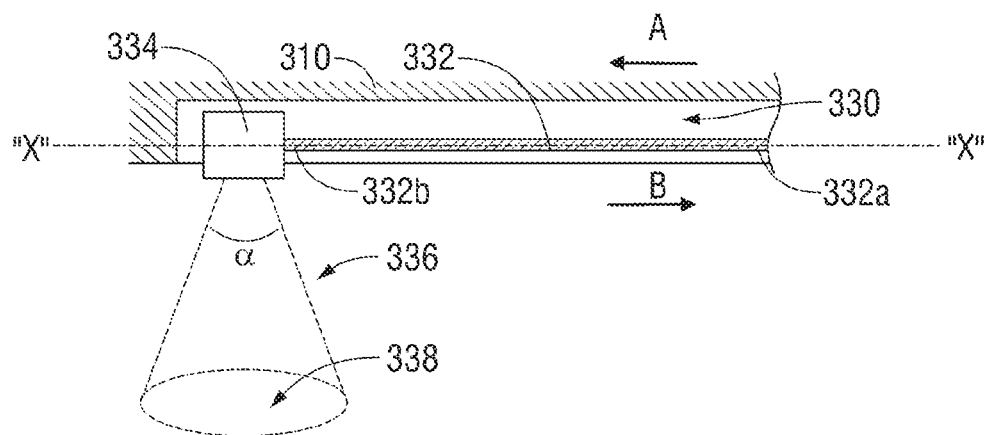
FIG. 4C is a side, schematic view of a laser fiber of the end effector assembly of FIG. 4A.

Referring now to FIGS. 4A-4C, illustrated is another embodiment of an end effector assembly 300. End effector assembly 300 includes jaw members 310 and 320 having proximal ends 310*a*, 320*a*, respectively, and distal ends 310*b*, 320*b*, respectively. Each jaw member 310 and 320 has a tissue contacting surface 312 and 322, respectively. In some embodiments, the tissue contacting surfaces 312 and 322 may include a transparent coating or cover disposed on the surface thereof, similar to the tissue contacting surfaces 112 and 122 of FIGS. 2A and 2B. Additionally, jaw member 310 includes a channel or groove 330 defined therealong that is configured to include a surgical treatment laser fiber 332 (e.g., sealing, cutting and/or sensing) having proximal and distal ends 332*a* and 332*b*. Surgical treatment laser fiber 332 is configured to translate along a longitudinal axis "X-X", defined within jaw member 310, and within channel 330. For example, surgical treatment laser fiber 332 may be translated from proximal end 310*a* to distal end 310*b* of jaw member 310 (e.g., in a distal direction "A") to cut, seal and/or sense tissue being grasped between jaw members 310 and 320. Additionally or alternatively, surgical treatment laser fiber 332 may be translated from distal end 310*b* to proximal end 310*a* of jaw member 310 (e.g., in a proximal direction "B") to cut, seal and/or sense tissue being grasped therebetween. It should be noted that surgical treatment laser fiber may be stationary within any one of the jaw members 310 and 320. In other embodiments, any other suitable type of light energy may be transmitted by the aforementioned fibers and should not only be limited to only laser light energy.

Referring to FIGS. 4A-4C, the distal end of laser fiber 332b includes a laser emitter 334 that is configured to emit a laser beam into a defined solid angle 336 forming a desired illumination pattern. Laser fiber 332 may be a so-called "end-firing" or "side-firing" laser fiber. The term "end-firing" as used herein denotes a laser fiber that has the capability to emit a light along a longitudinal axis "X-X" defined by jaw member 310. The term "side-firing" as used herein denotes a laser fiber that has the capability to emit light (or any other suitable light energy) that is non-parallel to the longitudinal axis "X-X" of jaw member 310. Laser emitter 334 may include various components, such as one or more reflective surfaces (e.g., mirrors), one or more optical fibers, one or more lenses, or any other suitable components for emitting and/or dispersing a laser beam. More particularly, laser emitter 334 is configured to emit light into the solid angle 336 that has an outer boundary that may be variable or predetermined. By varying or adjusting the solid angle 336, a laser target area 338 may be adjusted to vary the intensity of the laser light energy illuminating the tissue and the area of the tissue being treated, dissected or cut. Laser target area 338 may define any suitable target shape, for example, but not limited to an ellipse, rectangle, square and triangle. In some embodiments, laser emitter 334 may also be configured to seal and/or cut tissue grasped between the jaw members.

In addition to longitudinal movement of the laser emitter 334 along the longitudinal axis "X-X," the laser emitter 334 may also be rotated about the axis "X-X" and/or moved laterally (e.g., transverse) with respect thereto. Longitudinal, lateral, and rotational motion of the laser emitter 334 allows for directing light energy in any desired direction to accomplish desired tissue treatment effects.

Reflective groove(s) 340 may be made from a polished metal or a coating may be applied to the jaw member 320 if the jaw member 320 is formed from a non-metal and/or non-reflective material (e.g., plastic). The reflective groove 340 reflects laser light back through the tissue. Laser emitter 334 may receive the reflected laser light and transmit the signal back to generator 40 for processing. Various types of data may be integrated and calculated to render various outcomes or control tissue treatment based on the transmitted or reflected light.

Figure 5:
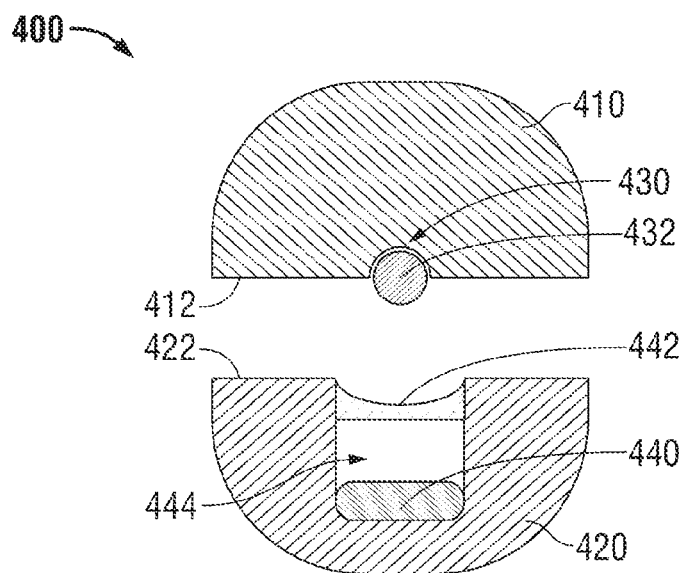
FIG. 5 is a front, cross-sectional view of an end effector assembly according to an embodiment of the present disclosure.

FIG. 5 illustrates another embodiment of an end effector assembly 400 for forming a desired illumination pattern. End effector assembly 400 includes jaw members 410 and 420 having tissue contacting surfaces 412 and 422. Similar to the above-described jaw members, jaw members 410 and 420 cooperate to grasp tissue therebetween. Jaw member 410 defines a channel or groove 430 therealong that is configured to include a laser fiber 432 that spans along jaw member 410 and is configured to emit a laser light within and along the length of jaw member 410. In some embodiments, the fiber 432 may be substituted by any laser source such as a fiber laser (e.g., tunable thalium fiber laser) described in this disclosure. In further embodiments, the tissue contacting surfaces 412 and 422 may include a transparent coating or cover disposed on the surface thereof, similar to the tissue contacting surfaces 112 and 122 of FIGS. 2A and 2B.

Jaw member 420 includes a receiving fiber 440 disposed within a cavity 444 defined therein that is configured to receive the laser light emitted from laser fiber 432. In some embodiments, the fiber 440 may be substituted by any optical detectors described in this disclosure or other suitable optical detectors. An optical window 442 is disposed along the surface of jaw member 420 between laser fiber 432 and receiving fiber 440. Optical window 442 may be any suitable type of optical lens configured to direct the laser light being emitted from laser fiber 432 to receiving fiber 440. Cavity 444 may be configured to contain a gas or any other medium to facilitate reception of laser light emitted by laser fiber 432 by receiving fiber 440.

Optical properties of tissue are known to change during heating. Properties such as the absorption coefficient ($\mu_a$), scattering coefficient ($\mu_s$), and anisotropy coefficient (g) have been shown to change as a function of temperature and time. These properties affect the transmission and reflection of light as it interacts with tissue. The present disclosure incorporates a receiving fiber 440 that may be used to detect and/or monitor changes in the transmission of laser light from laser fiber 432 through the tissue during a sealing cycle to determine when a desired tissue effect has been achieved. In this configuration, cut completion, e.g., when the tissue is separated, may also be detected and/or monitored using the receiving fiber 440.

Figure 6:
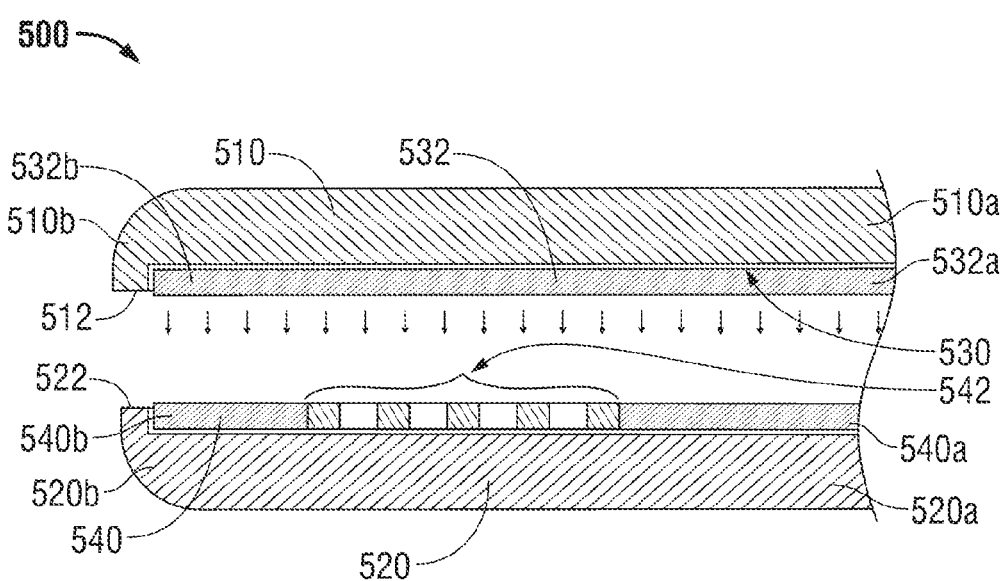
FIG. 6 is a side, cross-sectional view of an end effector assembly according to an embodiment of the present disclosure.

FIG. 6 illustrates another embodiment of an end effector assembly generally depicted as end effector assembly 500 for forming a desired illumination pattern. End effector assembly 500 includes jaw members 510 and 520 having tissue contacting surfaces 512 and 522. Similar to the above-described jaw members, jaw members 510 and 520 cooperate to grasp tissue therebetween. Additionally, jaw member 510 defines a channel or groove 530 therealong that is configured to include a laser cutting fiber 532 that spans between proximal and distal ends 532a and 532b of jaw member 510. Laser fiber 532 is configured to emit a laser light within and along the length of jaw members 510 and 520. On an opposing side, a receiving fiber 540 is disposed within jaw members 520 and extends along a length thereof and is configured to receive the laser light emitted from laser fiber 532.

Receiving fiber 540 includes proximal and distal ends 540a and 540b and also includes one or more sensors 542 therebetween. Sensor(s) 542 is configured to monitor a temperature during a seal cycle and provide feedback as to when a seal cycle is complete. Since pressure is a factor in the quality of a seal following a sealing treatment, sensor 542 may also determine jaw pressure by measuring the strain in the jaw members 510 and 520 resulting from applied mechanical loads when tissue is grasped between jaw members 510, 520. In this configuration, feedback may be provided to an operator as to whether the appropriate jaw pressure has been attained prior to energy activation to achieve a proper tissue seal and/or to the controller 42.

Figure 7A:
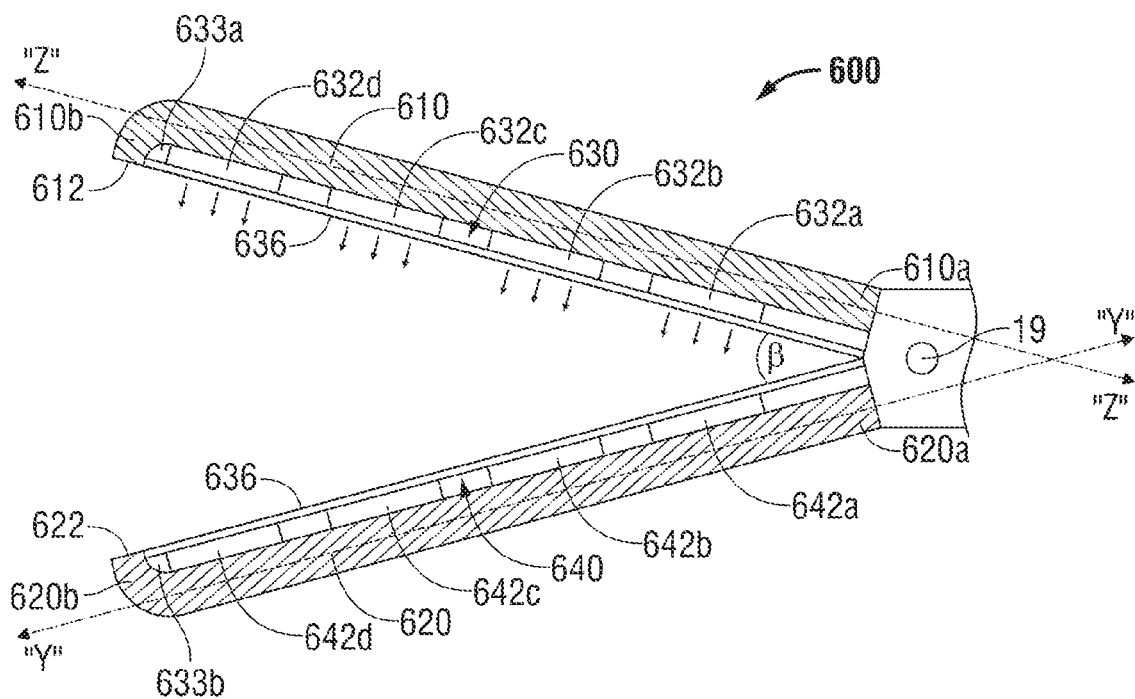
FIGS. 7A and 7B are side, cross-sectional views of an end effector assembly according to an embodiment of the present disclosure.
Figure 7B:
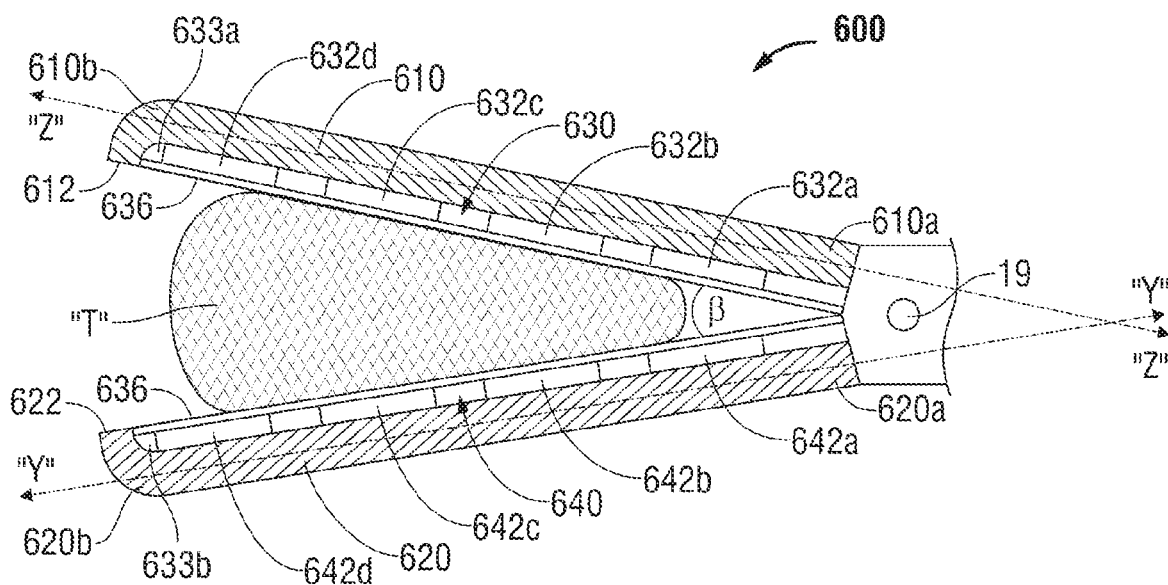

FIGS. 7A and 7B illustrate another embodiment of an end effector assembly 600 for forming a desired illumination pattern. End effector assembly 600 includes jaw members 610 and 620 having tissue contacting surfaces 612 and 622. Similar to the above-described jaw members, jaw members 610 and 620 cooperate to grasp tissue therebetween. Jaw members 610 and 620 each define longitudinal axes "Z-Z" and "Y-Y," respectively, that span from their respective proximal ends 610a, 620b to their respective distal ends 610b, 620b. Longitudinal axes "Z-Z" and "Y-Y" define an angle "β" that increases as jaw members 610 and 620 are separated from each other, when pivoted from a closed configuration to an open configuration.

End effector assembly 600 includes one or more light-emitting elements 632a, 632b, 632c, and 632d that are disposed within a channel 630 defined along the length of jaw member 610. Each light-emitting element 632a, 632b, 632c, and 632d is configured to emit a light energy within and along the length of jaw members 610 and 620. Light-emitting elements 632a, 632b, 632c, and 632d may be any suitable type of light-emitting element, for example, but not limited to high intensity LEDs configured for medical use and/or tissue treatment, optical fibers or other optical elements configured to emit light into the tissue. Light-emitting elements 632a, 632b, 632c, and 632d may be selectively activatable (e.g., one or a few at a time) and may emit light at different wavelengths. One or more light-receiving elements 642a, 642b, 642c, and 642d are disposed within a channel 640 defined along the length of jaw member 620. Each light-receiving element 642a, 642b, 642c, and 642d is configured to detect the light energy emitted from the light-emitting elements 632a, 632b, 632c, and 632d. The light-emitting elements 632a, 632b, 632c, and 632d and the light-receiving elements 642a, 642b, 642c, and 642d may be disposed behind a protective substrate 636 configured to transmit light.

The light-receiving elements 642a, 642b, 642c, and 642d may be any suitable light-receiving element, such as a lens, an optical fiber, or photodetector, and may be configured to measure optical properties of the tissue. In some embodiments, the light-receiving elements may collect and transmit light to optical systems configured to provide a variety of spectroscopic measurements including Raman spectroscopy, which is suitable for determining seal competition and identification of specific tissue types and its constituents (e.g., collagen, protein, water, etc.)

In some embodiments the light-receiving element 642a, 642b, 642c, and 642d and the light-emitting elements 632a, 632b, 632c, and 632d may be interspersed between the jaw members 610 and 620, such that each of the jaw members 610 and 620 includes one or more receiving modules and one or more light-emitting elements. This configuration provides for measuring optical properties (e.g., reflection and transmission data) at each jaw member 610 and 620 and allows for use of optical coherence tomography to obtain images of the tissue grasped between the jaw members 610 and 620. Other techniques for determining optical tissue properties are disclosed in a commonly-owned U.S. patent application Ser. No. 12/665,081 entitled "Method and System for Monitoring Tissue During an Electrosurgical Procedure," the entire contents of which is incorporated by reference herein.

Each light-emitting element 632a, 632b, 632c, and 632d may be configured to independently adjust its emittance of light energy along the jaw member 610 depending on angle "β". For example, when angle "β" is about 45 degrees (e.g., when jaw members 610 and 620 are moved towards an open configuration) the distal-most light-emitting element 632d may emit light energy with a greater intensity than the proximal-most light-emitting element 632a. As angle "β" decreases to about 2 degrees (e.g., when jaw members 610 and 620 are moved towards a closed configuration) light-emitting elements 632a, 632b, 632c, 632d are configured to emit light energy with substantially the same intensity.

Intensity of the light energy, including individual intensity as described above, transmitted through the light-emitting elements 632a, 632b, 632c, and 632d may be adjusted by the controller 42 based on the measured angle "β" and/or the gap distance between the jaw members 610 and 620. As used herein, the term "gap distance" as used herein denotes the distance between the tissue contacting surfaces 612 and 622. Since the jaw members 610 and 620 are pivotable relative to each other, the angle "β" therebetween is directly related to the gap distance and the two concepts are used interchangeably. Angle "β" may be measured using any suitable proximity sensors 633a, 633b disposed within the jaw members 610 and 620, respectively. The sensors 633a, 633b may be coupled to the controller 42 and include, but are not limited to, Hall Effect sensors, RF based sensors, and the like. In some embodiments, the sensors 633a, 633b may be a pair of corresponding light transmitter/receiver elements. In particular, a sensor may be a light emitting element (e.g., LED) paired with a photodetector (e.g., PIN diode).

In some embodiments, the angle "β" may be controlled to achieve a desired gap distance between the jaw members 610 and 620 to match the thickness of the tissue to the optical depth of the light energy. If the thickness of the tissue is not greater than the optical depth of the light being passed through the tissue, then the light energy is not going to be fully absorbed. This occurs if the tissue is compressed such that it is thinner than the optical depth of the light energy being used. In addition, if the tissue is not sufficiently compressed, light energy does not fully penetrate the compressed tissue resulting in non-uniform heating of the tissue. Controlling of the gap distance to substantially match the optical depth of the light energy with the thickness of the tissue ensures that light energy is optimally absorbed.

In some embodiments where the jaw members 610 and 620 include reflective surfaces, such as the jaw members 110 and 120, the angle "β" may also be controlled while taking into consideration the reflection of the light from the tissue contacting surfaces 612 and 622.

The controller 42 obtains the angle "β" from the sensors 633a, 633b and determines the gap distance based on the measurement. The controller 42 also obtains the wavelength of the light energy being delivered by the generator 40. This may be accomplished by storing a value of the wavelength in memory or any other computer-readable storage device which may be either transient (e.g., random access memory) or non-transient (e.g., flash memory). The controller 42 then calculates the desired gap distance based on the stored wavelength value and stored tissue properties. The controller 42 also compares the actual gap distance and/or angle "β" to desired gap distance and/or angle "β" as calculated based on the wavelength. Based on the comparison, the controller 42 may adjust the gap distance and/or angle "β" between the jaw members 610 and 620 automatically and/or output the difference for the user. Automatic adjustment may be accomplished by providing the jaw members 610 and 620 with automatic closure mechanisms such as those disclosed in commonly owned U.S. Pat. No. 7,491,202, entitled "Electrosurgical Forceps With Slow Closure Sealing Plates and Method of Sealing Tissue," which discloses automatic gap control for electrosurgical forceps, the entire contents of which is incorporated by reference herein.

For manual gap adjustment, the controller 42 may output the difference between actual and desired gap distance and/or angle "β" in an audio/visual manner. In some embodiments, the actual and desired gap distance and/or angle "β" or the difference therebetween may be represented numerically and/or graphically (e.g., color-coded). The difference may also be represented by audio alarms (e.g., adjusting frequency or amplitude of sound pulses).

As discussed in the previous embodiments, light-emitting elements 632a, 632b, 632c, and 632d and receiving modules 642a, 642b, 642c, and 642d may be configured to have optical sensing properties such that each pair of light-emitting element and receiving module (e.g., light-emitting element 632a and receiving module 642a) may be used to monitor the sealing process at a particular position. Light-emitting elements 632a, 632b, 632c, and 632d and receiving modules 642a, 642b, 642c, and 642d may also be configured to monitor the presence and state of other material in and around the sealing device and may also modify a sealing algorithm based upon the information collected.

In other embodiments, light-emitting elements 632a, 632b, 632c, and 632d and receiving modules 642a, 642b, 642c, and 642d may also be configured to inject a heat pulse and measure the response of tissue "T", measure spectral characteristics in transmission and/or reflection, measure spectral characteristics at different positions, measure spectral characteristics at different light frequencies. Light-emitting elements 632a, 632b, 632c, and 632d and receiving modules 642a, 642b, 642c, and 642d may also be configured to measure temperature at one or more locations between proximal and distal ends of jaw members 610 and 620.

Figure 8A:
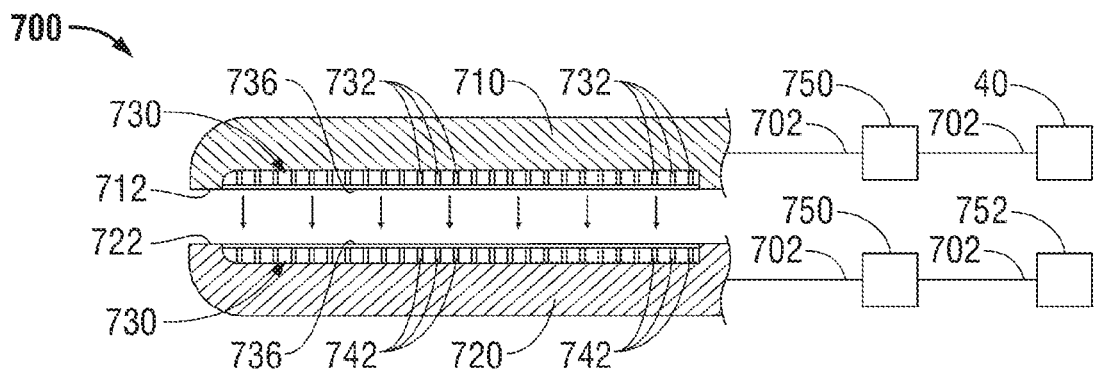
FIG. 8A is a side, cross-sectional view of an end effector assembly according to an embodiment of the present disclosure.
Figure 8B:
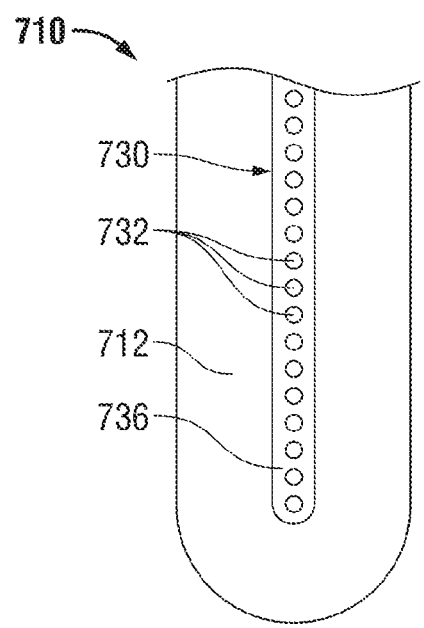
FIGS. 8B and 8C are top views of the end effector shown in FIG. 8A.
Figure 8C:
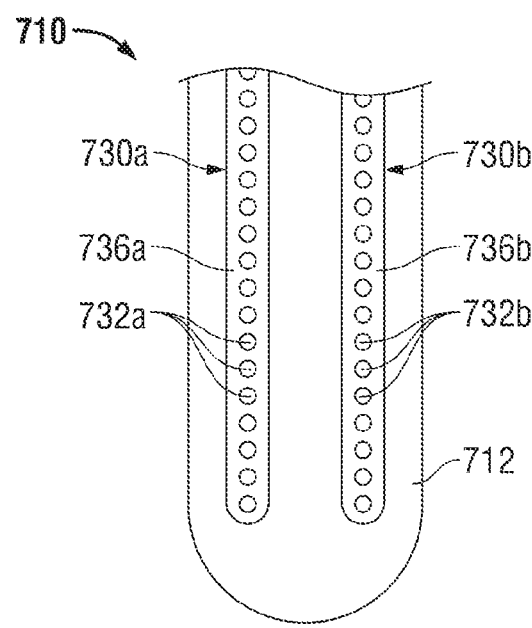

Referring now to FIGS. 8A-8C, another embodiment of an end effector assembly is shown as end effector assembly 700 for forming a desired illumination pattern. End effector assembly 700 includes jaw members 710 and 720 having tissue contacting surfaces 712 and 722. Similar to the above-described jaw members, jaw members 710 and 720 cooperate to grasp tissue therebetween. Jaw members 710, 720 are operably connected to generator 40 via an optical fiber 702 that provides light energy for treating tissue grasped between jaw members 710, 720.

Each jaw member 710, 720 includes one or more channels 730 having one or more vertically-aligned optical fibers 732 that are configured to emit and receive light energy from generator 40 via optical fiber 702. In some embodiments, optical fibers 732 of jaw member 710 are vertically-aligned with optical fibers 742 of jaw member 720 such that optical communication is established. That is, one of the optical fibers is a transmitting optical fiber (e.g., optical fiber 732) and the opposing fiber is a receiving optical fiber (e.g., optical fiber 742). Any number of transmitting optical fibers 732 may be disposed about jaw member 710. Additionally or alternatively, any number of transmitting optical fibers 742 may be disposed about jaw member 720. Thus, in other embodiments, vertical alignment of optical fibers 732 and 742 is not particularly necessary.

In some embodiments, end effector assembly 700 may also include one or more optical switches 750 that provide selective activation and detection of light energy to and from jaw members 710 and 720 by an operator and/or generator 40. Detection of light energy may be provided by an optical detector 752 or the like. In some embodiments, each channel 730 may be covered by a transparent cover 736 to allow optical communication between jaw members 710 and 720. It should be noted that any type of detecting device may be utilized with any of the embodiments presently disclose, for example, but not limited to photo diodes and charged coupled device (CCD) arrays.

FIG. 8B illustrates jaw member 710 having a single channel 730 defined therethrough that includes a plurality of optical fibers 732, as described above, that are covered by cover 736. Cover 736 may be any suitable material configured to allow optical communication between optical fibers 732 and 742. In another embodiment, FIG. 8C illustrates jaw member 710 defining a plurality of channels 730a and 730b therethrough and also includes a plurality of optical fibers 732 that are covered by cover 736.

Figure 9:
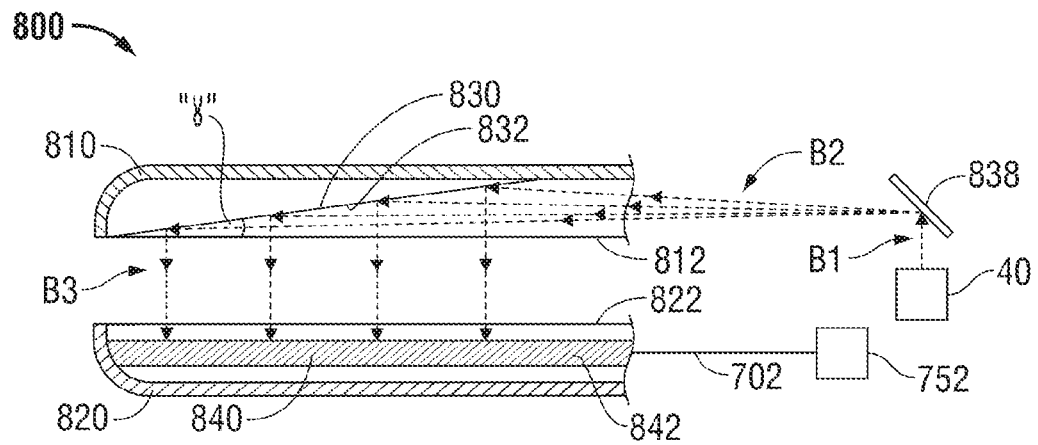
FIG. 9 is a side, cross-sectional view of an end effector assembly according to an embodiment of the present disclosure.

Referring now to FIG. 9, another embodiment of an end effector assembly is shown as end effector assembly 800 for forming a desired illumination pattern. End effector assembly 800 includes jaw members 810 and 820 having tissue contacting surfaces 812 and 822. Similar to the above-described jaw members, jaw members 810 and 820 cooperate to grasp tissue therebetween. Jaw members 810, 820 are operably connected to an energy source that provides light via generator 40.

Jaw member 810 includes an optical element 830 defined therethrough. Optical element 830 includes a reflective surface 832 that is configured to reflect light energy received from generator 40. In this embodiment, generator 40 is configured to emit a beam B1 (e.g., single beam) towards an optical deflector 838 (e.g., mirror). Optical deflector 838 is configured to reflect all or a substantial amount of beam B1 emitted by generator 40 as beam B2 towards the tissue to be treated.

Jaw member 820 is in optical communication via an optical fiber 702 with an optical detector 752 that is configured to optically communicate with optical receiving fiber 842. In this configuration, the position of jaw members 810 and 820 may be determined at any time by the optical information transmitted and received by jaw members 810 and 820. Optical detector 752 or any other logical circuitry (e.g., generator 40 and various sensors) within forceps 10, 10' translate the light beams B3 received by optical receiving fiber 842 to determine the position of the jaw members 810 and 820. Once closed, more intense light energy (or RF energy) may be emitted from generator 40 to heat tissue and optical fiber(s) 702 may be configured to communicate with optical detector 752 to provide feedback to generator 40.

Figure 10:
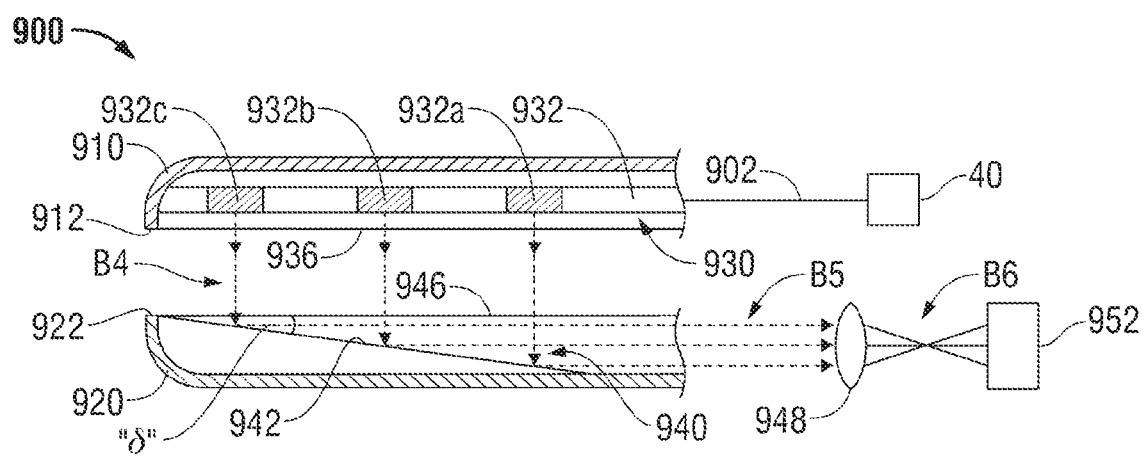
FIG. 10 is a side, cross-sectional view of an end effector assembly according to an embodiment of the present disclosure.

Referring now to FIG. 10, another embodiment of an end effector assembly is shown as end effector assembly 900 for forming a desired illumination pattern. End effector assembly 900 includes jaw members 910 and 920 having tissue contacting surfaces 912 and 922. Similar to the above-described jaw members, jaw members 910 and 920 cooperate to grasp tissue therebetween. Jaw members 910, 920 are operably connected to an energy source that provides light via generator 40.

In some embodiments, jaw members 910 and 920 define channels 930 and 940, respectively. Channel 930 includes an optical fiber 932 that is configured to emit light energy received from generator 40 via an optical fiber 902. Optical fiber 932 may be a diffusing fiber, as previously described in other embodiments. Additional or alternatively, optical transmitting fiber 932 may have transmitting light effectors 932a, 932b, 932c, that span along the length of channel 930, as shown in FIG. 10.

Channel 940 includes a reflective surface 942 that is configured to reflect light energy received from optical transmitting fiber 932 and/or transmitting light effectors 932a, 932b, and 932c of jaw member 910. In this embodiment, jaw member 910 is configured to emit one or more light beams B4, via optical light effectors 932a, 932b, 932c, such that reflective surface 942 reflects the light beams B4 into one or more light beams B5 toward an optical modifier (e.g., lens 948). It should be noted that reflective surface 942 is positioned along jaw member 920. In some embodiments, optical lens 948 may be disposed within channel 940 defined within jaw member 920.

Jaw member 920 is in optical communication via optical lens 948 with an image detector 952 that is configured to optically communicate with optical lens 948. In this configuration, the position of jaw members 910 and 920 may be determined at any time by the optical information transmitted and received by jaw members 910 and 920. That is, as the jaw 920 is pivoted with respect to the jaw 910, the reflective surface 942 is also moved relative to the light beams B4 causing the reflected light beams B5 to shift accordingly with respect to the lens 948. Image detector 952 or any other logical circuitry (e.g., generator 40 and various sensors) within forceps 10, 10' measures the intensity of the light passing through the tissue to determine position of the jaw members 910 and 920 and/or various tissue properties, as previously discussed in other embodiments. In another embodiment, the detector 952 may be used to image tissue, which may be post-processed by the image detector 952.

Figure 11:
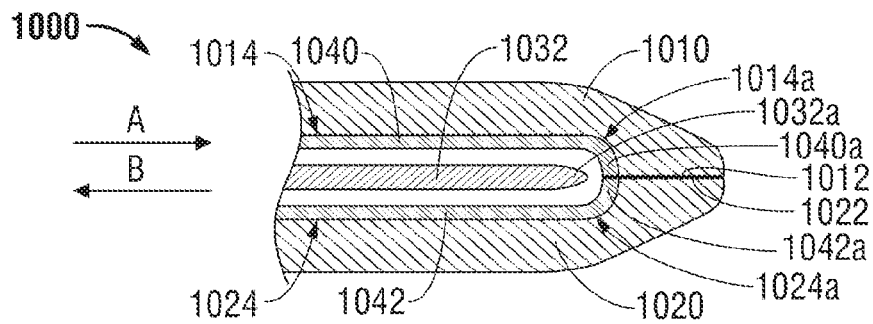
FIG. 11 is a side, cross-sectional view of an end effector assembly according to an embodiment of the present disclosure.
Figure 12A:
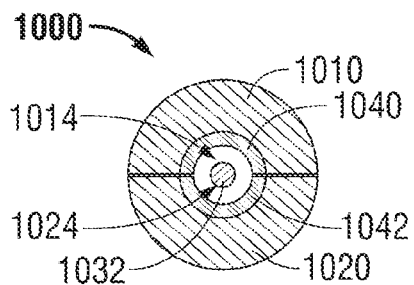
FIG. 12A is a front, cross-sectional view of the end effector assembly shown in FIG. 11.
Figure 12B:
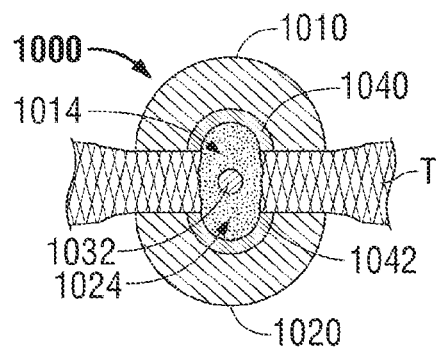
FIG. 12B is a front, cross-sectional view of the end effector assembly grasping tissue shown in FIG. 11.

FIGS. 11 and 12A and 12B show another embodiment of the presently disclosed end effector assembly generally shown as end effector assembly 1000 for forming a desired illumination pattern. End effector assembly 1000 includes jaw members 1010 and 1020 having tissue contacting surfaces 1012 and 1022. Similar to the above-described jaw members, jaw members 1010 and 1020 cooperate to grasp tissue therebetween. Jaw members 1010, 1020 are operably connected to an energy source (e.g., generator 40) that provides light energy. The light energy, as discussed above, may be provided in different forms, for example, but not limited to laser light, light emitting diode light, and any other suitable types of light energy.

In some embodiments, jaw members 1010 and 1020 define channels 1014 and 1024, respectively, therealong. Channels 1014 and 1024 together define an area such that an optical fiber 1032 is interposed and configured to emit light energy received from generator 40 via a delivery optical fiber (not shown). Optical fiber 1032 may be a diffusing crystal or fiber, as previously described in other embodiments. Additionally or alternatively, optical fiber 1032 may be initially disposed within shaft 12, 12' of surgical instrument 10, 10' and selectively translated in distal direction "A" and proximal direction "B" along a longitudinal axis defined by the jaw members 1010 and 1020. That is, optical fiber 1032 may be translated along the length of channels 1014 and 1024, as shown in FIG. 11. In some embodiments, optical fiber 1032 may be translated along the length of the jaw members 1010 and 1020 by trigger assembly 25, 25' (see FIGS. 1A and 1B).

Optical fiber 1032 is configured to have a cylindrical or conical shape that converges to a distal end 1032a. Distal end 1032a is configured to penetrate tissue as the optical fiber 1032 is translated in a distal direction between jaw members 1010 and 1020 and through tissue. In some embodiments, the optical fiber 1032 may be translated laterally and along tissue without penetrating tissue. The optical fiber 1032 may have any suitable shape, for example, but not limited to, rectangular, oval, and polygonal. In addition, distal end 1032a may also take the form of various suitable configurations (e.g., sharp or blunt).

With respect to FIG. 12A, channels 1014 and 1024 each include a reflective surface 1040 and 1042, respectively, that are each configured to reflect light energy received and/or emitted from optical fiber 1032. In this embodiment, optical fiber 1032 emits light energy in a radial direction (e.g., around the circumference of optical fiber 1032) such that reflective surfaces 1040 and 1042 receive the light energy emitted therefrom. In some embodiments, reflective surfaces 1040 and 1042 are each configured to wrap or coat the surface of their respective channels 1014, 1024. Reflective surfaces 1040 and 1042 may also include distal ends 1040a and 1042a, respectively, that curve along the converging distal ends 1014a and 1024a of channels 1014 and 1024. In this manner, light energy that is emitted from the distal end 1032a of optical fiber 1032 passes through the tissue and is reflected from distal ends 1040a and 1042a of reflected surfaces 1040 and 1042 and onto tissue grasped between jaws 1010 and 1020.

As shown in FIG. 12B, the optical fiber 1032 may also be used for cutting. Optical fiber 1032 is translated between jaw members 1010 and 1020 via channels 1014 and 1024 whereby light energy is selectively emitted to cut or sever the tissue by the light energy emitted by optical fiber 1032. In some embodiments, the optical fiber 1032 is configured to pierce the tissue grasped between jaw members 110 and 1020 to thereby emit light energy from within or inside the tissue surface (e.g., a first dose) and radiate light energy throughout the tissue grasped therebetween. This configuration may also be used to seal tissue by compressing tissue as discussed in some embodiments above.

Figure 13:
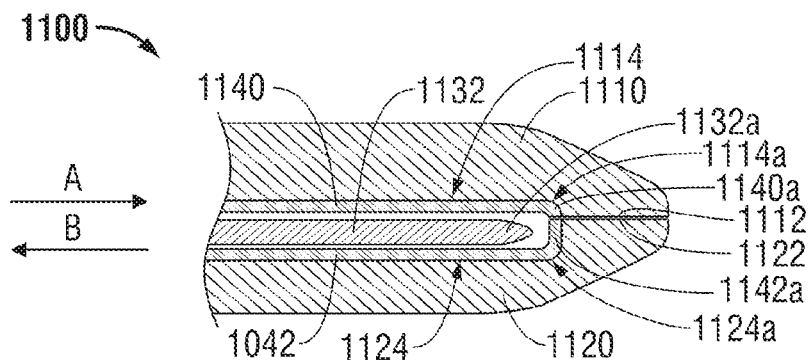
FIG. 13 is a side, cross-sectional view of an end effector assembly according to an embodiment of the present disclosure.
Figure 14:
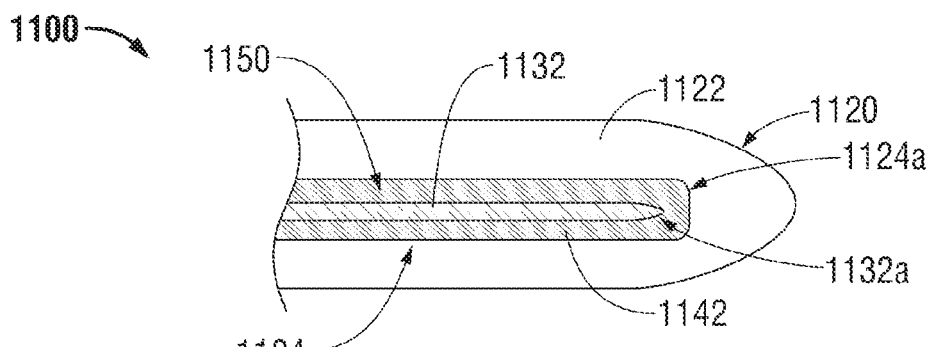
FIG. 14 is a top view of a jaw member of the end effector assembly shown in FIG. 13 according to an embodiment of the present disclosure.

Referring now to FIGS. 13 and 14, another embodiment of an end effector assembly is generally shown as end effector assembly 1100. End effector assembly 1100 includes jaw members 1110 and 1120 having tissue contacting surfaces 1112 and 1122. Similar to the above-described jaw members 110 and 120, jaw members 1110 and 1120 cooperate to grasp tissue therebetween. Jaw members 1110, 1120 are operably connected to an energy source (e.g., generator 40) that provides light energy.

In some embodiments, jaw members 1110 and 1120 include channels 1114 and 1124, respectively, defined therein and therealong. Channel 1124 includes an optical fiber 1132 that is configured to emit light energy received from generator 40 via a delivery optical fiber (not shown). The channel 1124 is shown as having a larger depth than the channel 1114, unlike channels 1014 and 1024, which have substantially similar dimensions. This configuration fully encloses the fiber 1132 within the jaw member 1120 allowing lateral translation of the optical fiber 1132 along the tissue surface to enable sealing and/or cutting of the tissue without penetrating tissue.

Optical fiber 1132 may be a diffusing fiber, as previously described in other embodiments. Additionally or alternatively, optical fiber 1132 may be initially disposed within shaft 12, 12' of surgical instrument 10, 10' and selectively translated in a distal direction "A" and proximal direction "B". That is, optical fiber 1132 may translate along the length of channel 1124, as shown in FIG. 13. Optical fiber 1132 may be selectively translated along the length of the jaw members 1110 and 1120 by trigger assembly 25, 25' (see FIGS. 1A and 1B). Alternatively, optical fiber 1132 may be stationary and fixed within channel 1124 such that optical fiber 1132 does not move in any direction.

Optical fiber 1132 may be configured to have, for example, a cylindrical shape that terminates to a distal end 1132a. Optical fiber 1132 may also take the form of other suitable shapes such as rectangular, oval, and polygonal. Accordingly, channel 1124 may also take the form of the shape of optical fiber 1132. In this manner, optical fiber 1132 may have a geometric fit with its respective channel 1124.

Channels 1114 and 1124 each include a reflective surface 1140 and 1142, respectively, that are each configured to reflect light energy received and/or emitted from optical fiber 1132. In this example embodiment, optical fiber 1132 emits light energy in a radial direction (e.g., around the circumference of optical fiber 1132) such that reflective surfaces 1140 and 1142 receive the light energy being emitted therefrom. Reflective surfaces 1140 and 1142 are each configured to wrap or coat the surface of their respective channel 1114, 1124. Reflective surfaces 1140 and 1142 may also include distal ends 1140a and 1142a, respectively, that curve along the converging distal ends 1114a and 1124a of channels 1114 and 1124. In this manner, light energy that is emitted from the distal end 1132a of optical fiber 1132 is reflected from distal ends 1140a and 1142a of reflected surfaces 1140 and 1142 and onto tissue that is grasped between jaws 1110 and 1120. In this embodiment, optical fiber 1132 may be configured to reside entirely within channel 1124 of jaw member 1120. Likewise, channel 1114 may be shallowly defined in jaw member 1110.

In use, the optical fiber 1132 is selectively translated within channel 1124 to divide tissue. Moreover, when jaw members 1110 and 1120 are closed and grasp tissue, the tissue is forced into channel 1124 to facilitate separation. Alternatively, optical fiber 1132 may be disposed in a deployed state within channel 1124 during tissue treatment. Once tissue is treated with light energy, optical fiber 1132 may be retracted to sever tissue.

Referring now to FIG. 14, which shows a plan view of the tissue contacting surface 1112, a window 1150 may be disposed atop of channel 1124 since the channel 1124 fully encloses the optical fiber 1132. Window 1150 is configured to enclose optical fiber 1132, reflective surface 1142 and channel 1124 to prevent tissue and surgical debris from entering therewithin. Window 1150 is also configured to allow light energy emitted from optical fiber 1132 to pass therethrough to treat tissue grasped between jaw members 1110 and 1120. Window 1150 may be manufactured from any suitable clear material, for example, but not limited to glass.

Turning now to FIGS. 15A-15D, one embodiment of an endoscopic forceps 2010 is shown for use with various surgical procedures. For the purposes herein, a vessel sealing forceps is shown and described, however, it is envisioned that other types of forceps or scissors may be utilized which both treat tissue for cauterization, coagulation or other purposes and as described above. Moreover, although the figure drawings depict a forceps 2010 for use in connection with endoscopic surgical procedures, the present disclosure may be used for more traditional open surgical procedures. For the purposes herein, the forceps 2010 is described in terms of an endoscopic instrument; however, it is contemplated that an open version of the forceps 2010 may also include the same or similar operating components and features as described above with respect to FIG. 1B.

Forceps 2010 generally includes a housing 2020, a handle assembly 2030, a rotating assembly 2080, a trigger assembly 2070 and an end effector assembly 2100 which mutually cooperate to grasp, treat and divide tissue. For the purposes herein, the handle assembly 2030, rotating assembly, trigger assembly 2070 and end effector assembly 100, which are described in more detail above with respect to FIGS. 1A-1C.

Figure 15A:
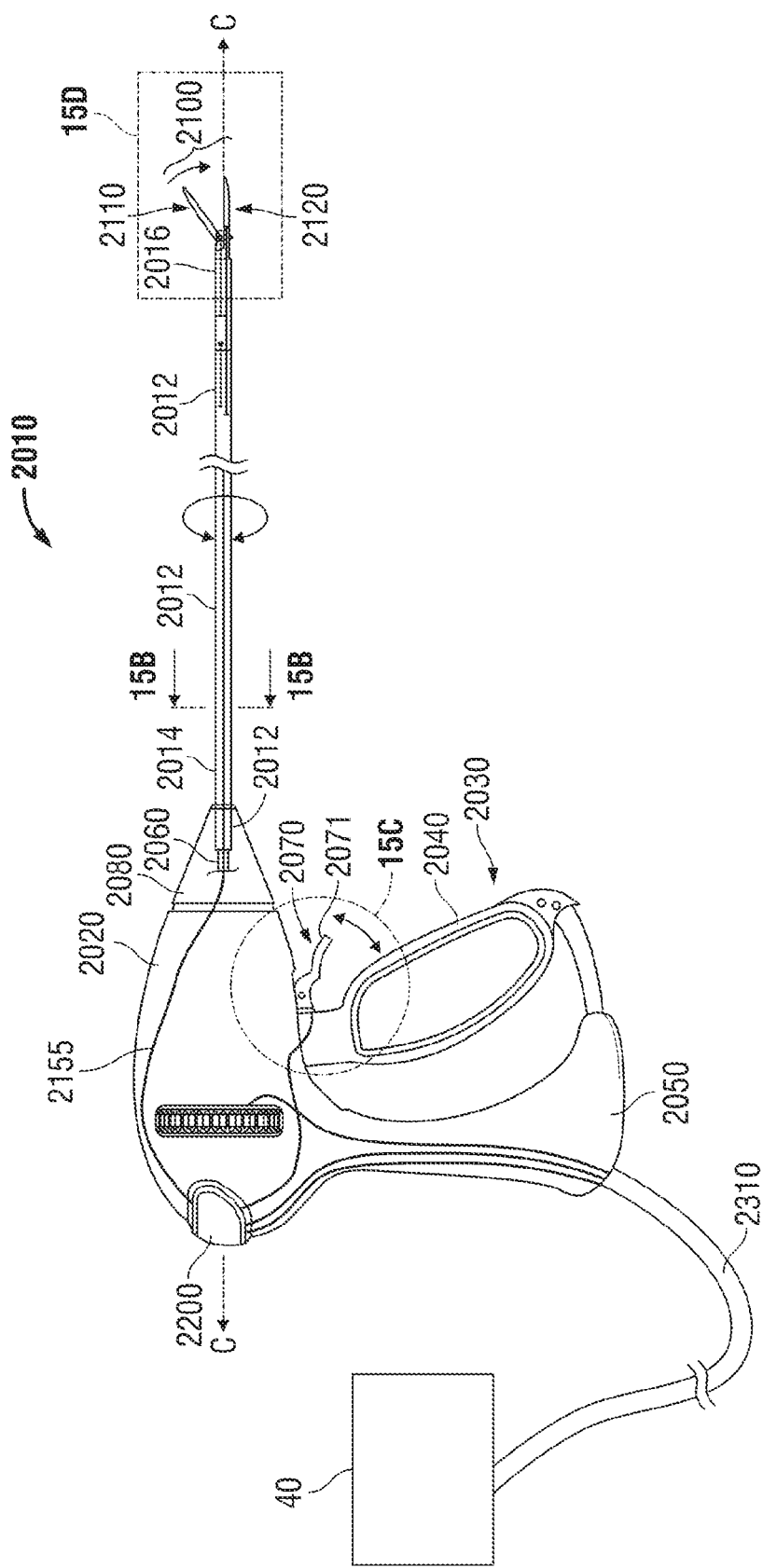
FIG. 15A is a side view of an endoscopic forceps showing a housing, a shaft, an end effector assembly and a trigger assembly in a first position according to an embodiment of the present disclosure.

Forceps 2010 includes a shaft 2012 which has a distal end 2016 dimensioned to mechanically engage the end effector assembly 2100 and a proximal end 2014 which mechanically engages the housing 2020. As best seen in FIG. 15A, forceps 10 also includes a cable 2310 which connects the forceps 2010 to a source of energy, e.g., the generator 40. Cable 2310 is internally divided into cable leads suitable for supplying power to the end effector 2100 including, but not limited to optical fibers, electrical leads, and the like.

Handle assembly 2030 includes a fixed handle 2050 and a movable handle 2040. Fixed handle 2050 is integrally associated with housing 2020 and handle 2040 is movable relative to fixed handle 2050. Rotating assembly 2080 may be integrally associated with the housing 2020 and is rotatable approximately 180 degrees in either direction about a longitudinal axis "C-C."

As mentioned above, end effector assembly 2100 is attached at the distal end 2016 of shaft 2012 and includes a pair of opposing jaw members 2110 and 2120. Movable handle 2040 of handle assembly 2030 is ultimately connected to an internally-disposed drive assembly (not shown) which, together, mechanically cooperate to impart movement of the jaw members 2110 and 2120 from an open position wherein the jaw members 2110 and 2120 are disposed in spaced relation relative to one another, to a clamping or closed position wherein the jaw members 2110 and 2120 cooperate to grasp tissue therebetween.

Figure 15B:
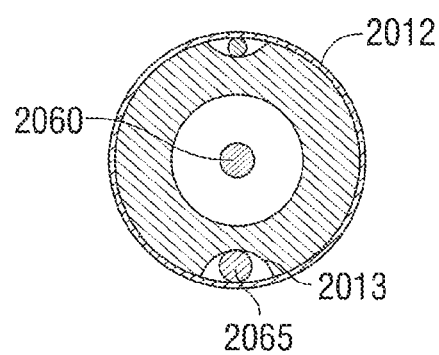
FIG. 15B is an enlarged, cross section taken along line 15B-15B of FIG. 15A according to an embodiment of the present disclosure.
Figure 15C:
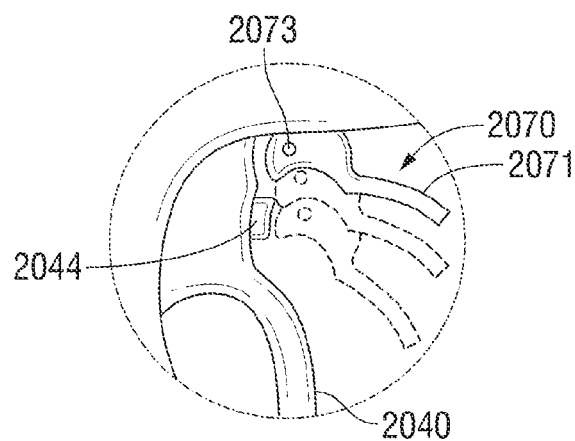
FIG. 15C is an enlarged, side view of the trigger assembly of FIG. 15A according to an embodiment of the present disclosure.
Figure 15D:
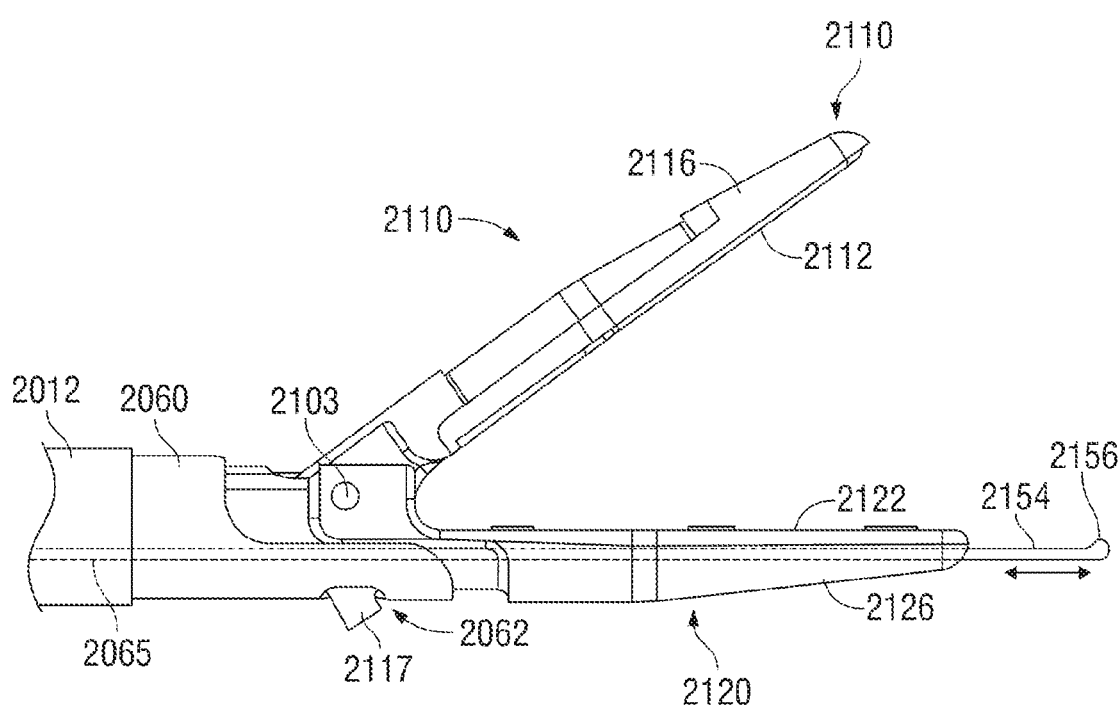
FIG. 15D is an enlarged, side view of the embodiment of an end effector assembly of FIG. 15A showing relative extension of a light dissection element from a distal end of the end effector assembly according to an embodiment of the present disclosure.
Figure 16:
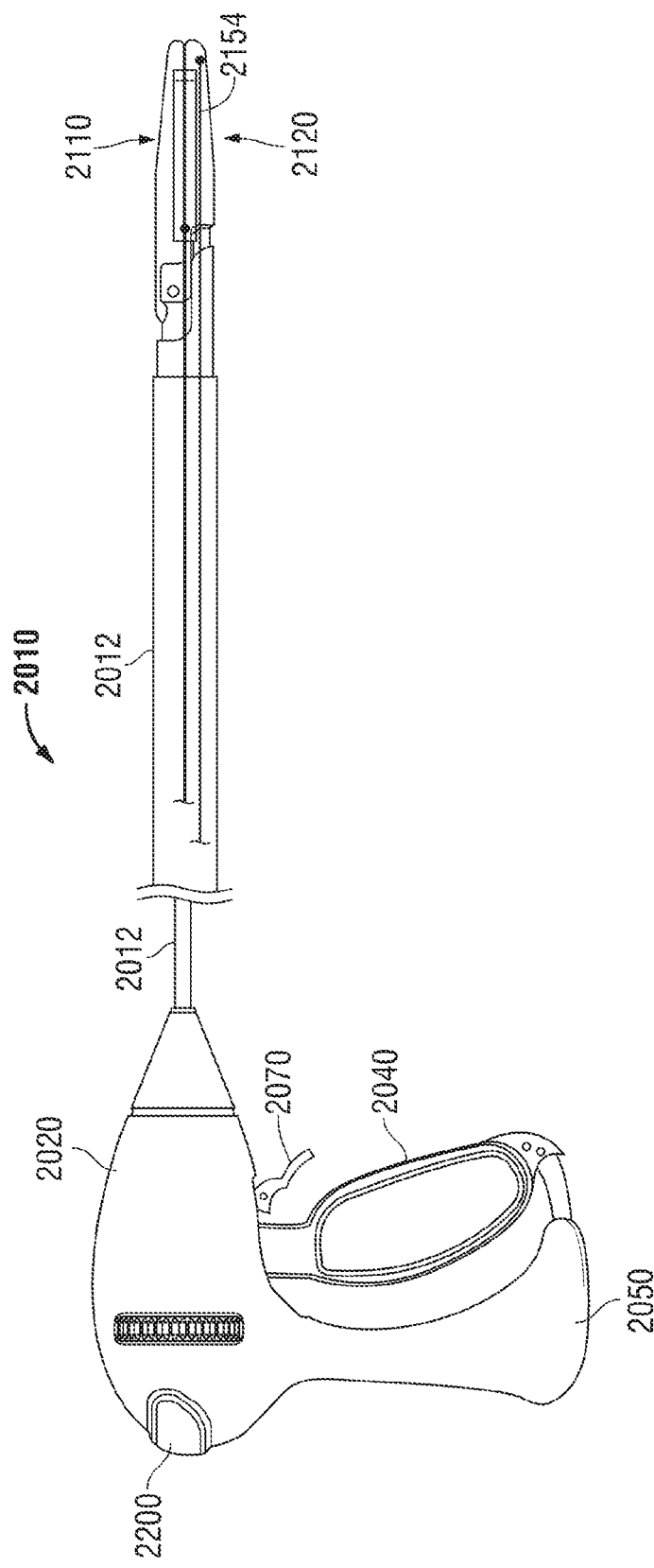
FIGS. 16 and 17 are side views of the trigger assembly for extending a light dissection element shown from a distal end of the end effector assembly according to an embodiment of the present disclosure.
Figure 17:
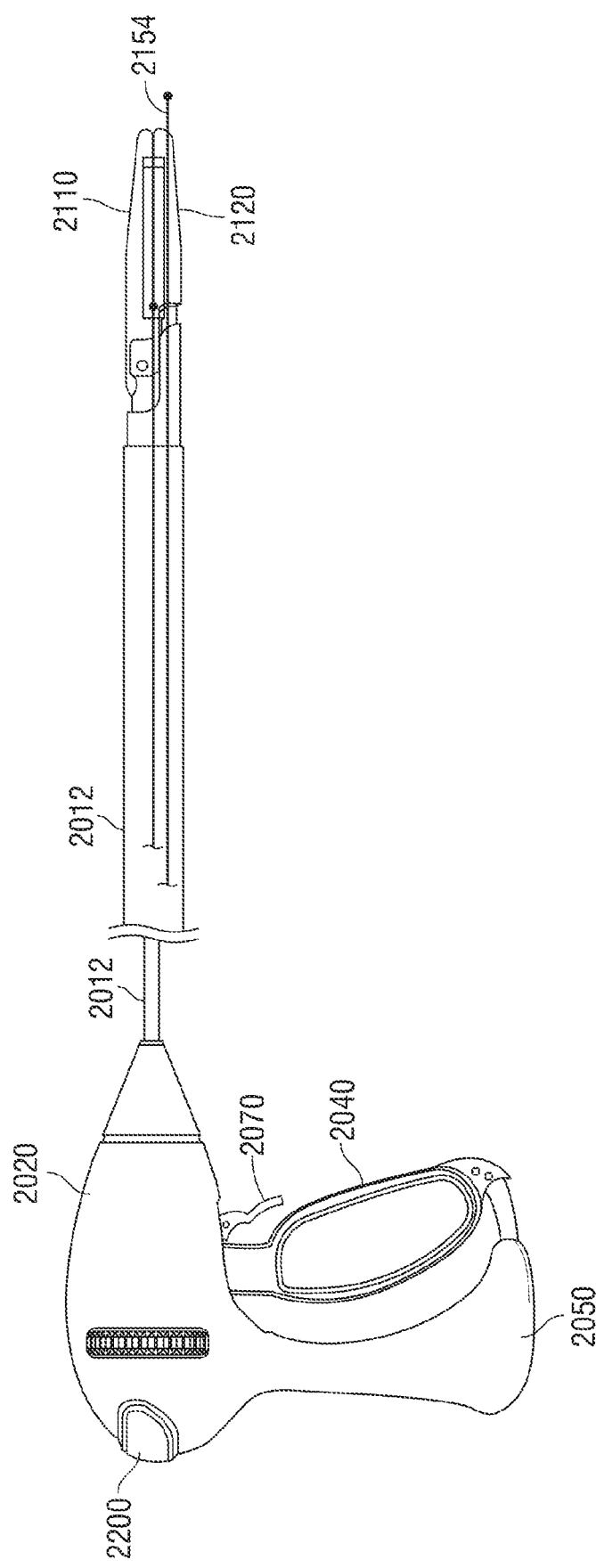
Figure 20:
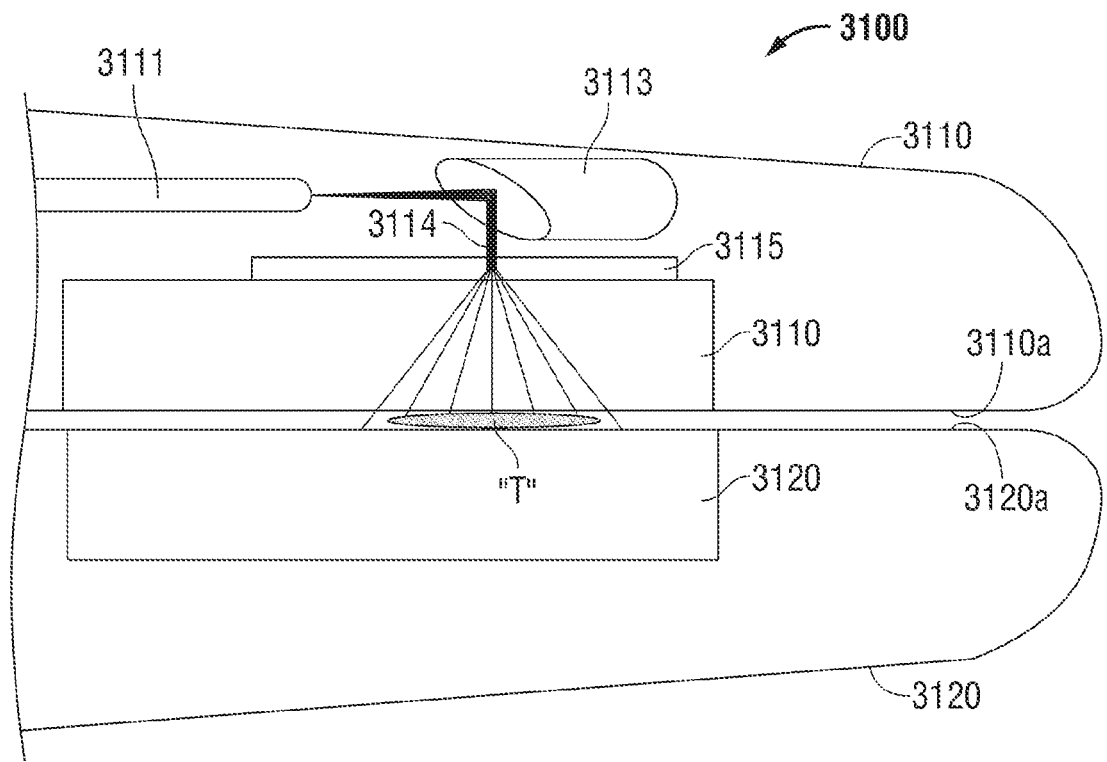
FIG. 20 is a side, cross-sectional view of an end effector assembly according to an embodiment of the present disclosure.

Turning now to the more detailed features of one embodiment of the present disclosure as described with respect to FIGS. 15A-16. As best seen in FIGS. 15A and 15D, the end effector assembly 2100 includes opposing jaw members 2110 and 2120 which cooperate to effectively grasp tissue for sealing purposes. The end effector assembly 2100 is designed as a unilateral assembly, i.e., jaw member 2120 is fixed relative to the shaft 2012 and jaw member 2110 pivots about a pivot pin 2103 to grasp tissue.

As best shown in FIG. 15D, each of the jaw members 2110 and 2120 includes a jaw housing 2116 and 2126 and a tissue sealing surface 2112 and 2122, respectively. The tissue sealing surfaces 2112 and 2122 may incorporate any of the light energy sealing members discussed above with respect to FIGS. 1-14.

More particularly, the unilateral end effector assembly 2100 includes one stationary or fixed jaw member 2120 mounted in fixed relation to the shaft 2012 and pivoting jaw member 2110 mounted about a pivot pin 2103 attached to the stationary jaw member 2120. A reciprocating sleeve 2060 is slidingly disposed within the shaft 2012 and is remotely operable by the drive assembly (not shown) which cooperates with handle 2040 as explained above to open and close the jaw members 2110 and 2120. The pivoting jaw member 2110 includes a detent or protrusion 2117 which extends from jaw member 2110 through an aperture 2062 disposed within the reciprocating sleeve 2060 (FIG. 15D). The pivoting jaw member 2110 is actuated by sliding the sleeve 2060 axially within the shaft 2012 such that aperture 2062 abuts against the detent 2117 on the pivoting jaw member 2110. Pulling the sleeve 2060 proximally closes the jaw members 2110 and 2120 about tissue grasped therebetween and pushing the sleeve 2060 distally opens the jaw members 2110 and 2120 for approximating and grasping purposes.

Once actuated, handle 2040 moves in a generally arcuate fashion towards fixed handle 2050 about the pivot point which forces the driving flange (not shown) proximally against the drive assembly (not shown) which, in turn, pulls reciprocating sleeve 2060 in a generally proximal direction to close jaw member 2110 relative to jaw member 120. Moreover, proximal rotation of the handle 2040 causes the locking flange 2044 to release, i.e., "unlock" the trigger assembly 2070 for selective actuation.

Turning now to the operating characteristics of the present disclosure and as seen in the majority of the figures, forceps 2010 is designed for both sealing of tissue (either by vessel sealing as described above or coagulation or cauterization with other similar instruments) and dissection of tissue. For example, FIGS. 15A-D and 16-18 show one embodiment of a forceps 2010 which includes a light dissection element 2154 which may be selectively extended and selectively activated to treat tissue.

The dissection element 2154 is coupled to the generator 40 via an optical fiber 2155. The optical fiber 2155 is disposed within the cable 2310. The dissection element 2154 also includes a dissection tip 2156. In some embodiments, the dissection tip 2156 may be formed from any suitable light transmissive materials including, but not limited to synthetic sapphire and the like. The dissection tip 2156 may have any suitable shape for transmitting and/or focusing light energy including, but not limited to, conical, frusto-conical, pyramidal, cylindrical, any other granulated surfaced, combinations thereof, and the like.

FIGS. 15A-15D and 16-18 show one embodiment wherein the dissection element 2154 is housed for selective extension within one jaw member, e.g., jaw member 2120, of the end effector assembly 2100. More particularly, dissection element 2154 is designed to move independently from a knife assembly 2180 and may be extended by further proximal movement of the trigger assembly 2070 (FIGS. 15A, 16 and 17) or by a separate actuator 2450 (FIG. 18).

As best shown in FIGS. 15A and 15C, trigger assembly 2070 mounts atop movable handle 2040 and cooperates with dissection element 2154 (FIGS. 16-17) to selectively translate dissection element 2154 through tissue. More particularly, the trigger assembly 2070 includes a finger actuator 2071 and a pivot pin 2073 which mounts the trigger assembly 2070 to the housing 2020. Finger actuator 2071 is dimensioned to abut the locking flange 2044 on handle 2040 when the handle 2040 is disposed in a non-actuated position, i.e., the jaw members 2110 and 2120 are opened.

In some embodiments, the dissection element 2154 is connected to a reciprocating rod 2065 which extends through an elongated notch 2013 in the outer periphery of the shaft 2012 as best seen in FIG. 15B. The trigger assembly 2070 may be designed such that the dissection element 2154 may be extended when the jaw members 2110 and 2120 are in the open or closed position. For example, the trigger 2071 may be moved distally (or upwardly) from its original, rested, neutral or pre-actuated position to advance the dissection element 2154. Alternatively, the dissection element 2154 may be advanced irrespective of the orientation of the jaw members 2110 and 2120. For example, the trigger assembly 2070 could be designed such that the it can be moved laterally (i.e., perpendicular to the longitudinal axis "C") to advance the dissection element 2154 or the trigger assembly 2070 could be designed such that the dissection element 2154 is extendible when the trigger 2071 is moved to a proximal-most position (i.e., past the "cut" position as described above) and/or when the trigger 2071 is advanced distally from the neutral or pre-actuated orientation. A return spring (not shown) may be included to return the dissection element 2154 to a non-extended position upon release of the trigger 2071.

Upon extension of the dissection element 2154, the generator 2300 is configured to automatically switch the forceps 2010 from a sealing mode (i.e., deactivating energy delivery to jaw members 2110 and 2120) to an optical dissection activation mode (i.e., activating the dissection element 2154).

As described above, when the forceps 2010 is configured for sealing operation, the activation of switch 2200 transfers energy from jaw members 2110 and/or jaw member 2120 to seal tissue. In the dissection mode, activation of switch 2200 (or a separate switch, e.g., a footswitch), supplies light energy to the dissection element 2154. Activation of the dissection element 2154 allows a surgeon to quickly treat avascular tissue structures and/or quickly dissect narrow tissue planes.

In some embodiments, the trigger assembly 2070 may also be configured to transmit light energy to the dissection element 2154 when extended. For example, the trigger assembly 2070 may be configured such that proximal-most actuation of the trigger 2071 (FIG. 15C) both extends and activates the dissection element 2154. An automatic safety circuit (not shown) may be employed which prevents the switch 200 from supplying light energy to the jaw members 2110 and 2120 when the dissection element 2154 is extended.

In some embodiments, the dissection element 2145 may be disposed within one of the jaw members 2110 and 2120 and may be selectively activated via the switch 2200. As shown in FIGS. 18A and 18B, in further embodiments, a light dissection element 2445 may be disposed on an outer periphery of one of the jaw members 2110 and 2120. For sake of simplicity only a single jaw member, namely, the jaw member 2110 is going to be discussed.

The dissection member 2445 may be a light diffusing element, such as the light diffuser 132 described above with respect to FIGS. 2A and 2B. The dissection member 2445 is coupled via an optical fiber 2446 to the generator 40 and is disposed on or along at least a portion of an outer periphery 2110a of the jaw member 2110. The term "outer periphery" denotes any surface of the jaw member 2110, such as the jaw housing 2116, that is not a tissue sealing contact surface 2112 or 2122. The dissection member 2445 may be selectively activated via the switch 2200 similar to the dissection member 2145 and may incorporate similar features, e.g., preventing light energy from being transmitted to the sealing surfaces 2112 and 2122 as described above with respect to the dissection member 2145.

Referring now to FIG. 19, another embodiment of an end effector assembly is shown as end effector assembly 1900 for forming a desired illumination pattern. End effector assembly 1900 includes jaw members 1910 and 1920 having tissue contacting surfaces 1912 and 1922. Similar to the above-described jaw members, jaw members 1910 and 1920 cooperate to grasp tissue therebetween. Jaw members 1910, 1920 are operably connected via an optical fiber 1911 to a light energy source (e.g., generator 40). In particular, the optical fiber 1911 is coupled to the jaw member 1910. The light may be provided in different forms, including, but not limited to lasers, light emitting diode, and any other suitable type of light energy.

The jaw member 1910 is formed from an optically transmissive material having an outer reflective coating 1910a. The transmissive material may be an optically diffusing material, such as, frosted sapphire crystal or an optically scattering material, such as polyoxymethylene, which is sold under a trademark DELRIN®, available from DuPont, Wilmington, Del. The light from the optical fiber 1911 is transmitted to the jaw member 1910 and is contained therein by the reflective coating 1910a. This prevents the light from escaping outside the jaw member 1910 other than through the tissue contacting surface 1912.

The jaw member 1920 may be formed from any optically absorbent or reflective tissue material. In some embodiments, the jaw member 1920 may include an optically absorbent or reflective coating 1920a on the tissue contacting surface 1922. The coating 1920a and/or the jaw member 1920 block the light from passing through the jaw member 1920 concentrating the light energy at the tissue grasped between the jaw members 1910 and 1920.

Referring now to FIGS. 20-24, another embodiment of an end effector assembly is shown as end effector assembly 3100 for forming a desired illumination pattern. End effector assembly 3100 includes jaw members 3110 and 3120 having tissue contacting members 3112 and 3122, defining tissue contacting surfaces 3112a and 3122a, respectively. Similar to the above-described jaw members, jaw members 3110 and 3120 cooperate to grasp tissue "T" therebetween. Jaw members 3110, 3120 are operably connected via an optical fiber 3111 to a light energy source (e.g., generator 40). In particular, the optical fiber 3111 is coupled to the jaw member 3110. The light may be provided in different forms, including, but not limited to lasers, light emitting diode, and any other suitable type of light energy.

The tissue contacting member 3112 may be formed from an optically transmissive material, which may be an optically diffusing material, such as, frosted sapphire crystal or an optically scattering material, such as polyoxymethylene, which is sold under a trademark DELRIN®, available from DuPont, Wilmington, Del. The tissue contacting member 3122 may also be formed from a similar material as the tissue contacting member 3112. In some embodiments, the tissue contacting member 3122 may be formed any optically absorbent or reflective tissue material.

Figure 21:
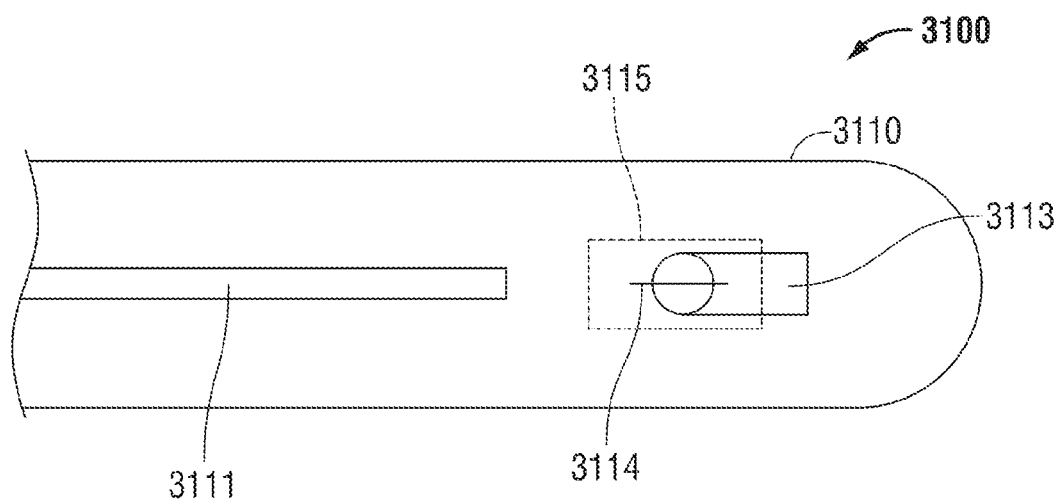
FIG. 21 is a top, cross-sectional view of a top jaw member of the end effector of FIG. 20.

The jaw member 3110 further includes a cylindrical lens 3113 for focusing the light transmitted by the fiber 3111 toward the tissue contacting surface 3112a in a line of light 3114. FIG. 21 shows a top view of the jaw member 3110. In some embodiments, the light is reflected at approximately 90° angle. This angle may be of any suitable amount and depends on the position of the fiber 3111 to the tissue contacting surface 3112a.

The focused light from the lens is then passed through a diffraction grating 3115 which is disposed between the lens 3113 and the tissue contacting member 3112. The diffraction grating 3115 is configured to separate the line of light 3114 into two or more light beams 3116a, 3116b, 3116c based on a plurality of through lines 3117 disposed therein as shown in FIGS. 22 and 23.

Figure 22:
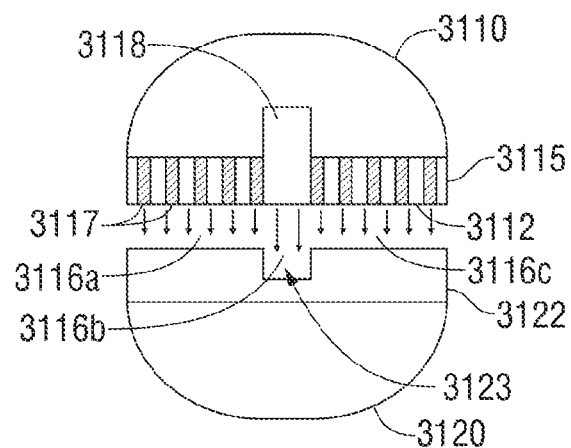
FIG. 22 is a front, cross-sectional view of the end effector assembly of FIG. 20 according to an embodiment of the present disclosure.
Figure 23:
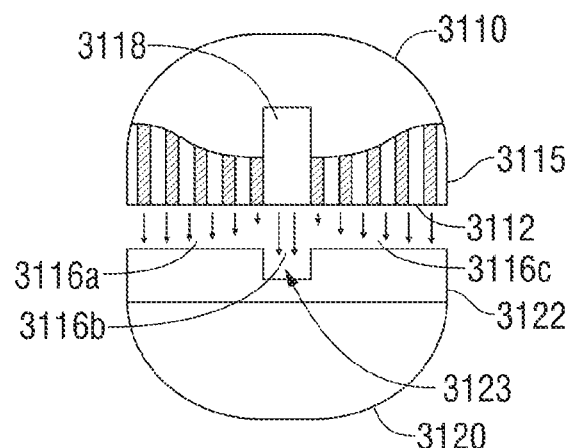
FIG. 23 is a front, cross-sectional view of the end effector assembly of FIG. 20 according to an embodiment of the present disclosure.
Figure 24:
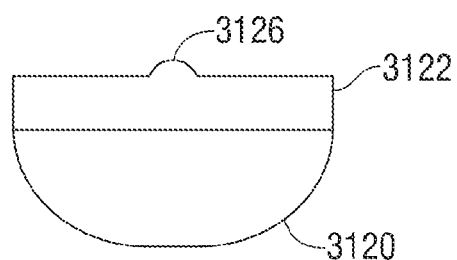
FIG. 24 is a front, cross-sectional view of a bottom jaw member of the end effector assembly of FIG. 20 according to an embodiment of the present disclosure.

As shown in FIGS. 22 and 23, the diffraction grating 3115 also includes a centrally disposed cutting slit 3118. The diffraction grating 3115 may generate three light beams 3116a, 3116b, 3116c. The light beams 3116a and 3116c are produced on the periphery of the jaw members 3110, 3120 as they pass through the grating 3115. The light beam 3116b passes through the cutting slit 3118 and has higher intensity than the light beams 3116a and 3116c. The light beams 3116a and 3116c are suitable for sealing tissue due to their lower intensity, whereas the light beam 3116c is more suitable for cutting tissue due to its higher intensity. The tissue contacting member 3122 of the jaw member 3120 includes a cutting channel 3123 disposed therein, which aligns with the cutting slit 3118. In some embodiments, the tissue contacting member 3122 may have a flat, unaltered surface. In further embodiments, as illustrated in FIG. 24, the tissue contacting member 3122 may have a protruding member 3126 centrally disposed on the tissue contacting surface 3122a to provide additional pressure on the tissue grasped between the jaw members 3110 and 3120. The protrusion member 3126 may have absorption properties to heat faster and enhance cutting.

Light energy is suitable for sealing tissue since it is converted into heat energy by absorption at a molecular level. In particular, certain molecules absorb light at certain wavelengths. In addition, as tissue is treated it undergoes physical and chemical changes, thus the wavelength at which light is optimally absorbed also changes. In some embodiments, light energy may be provided at two or more wavelengths to provide light energy that is optimally absorbed by two or more molecules (e.g., tissue types).

Figure 25:
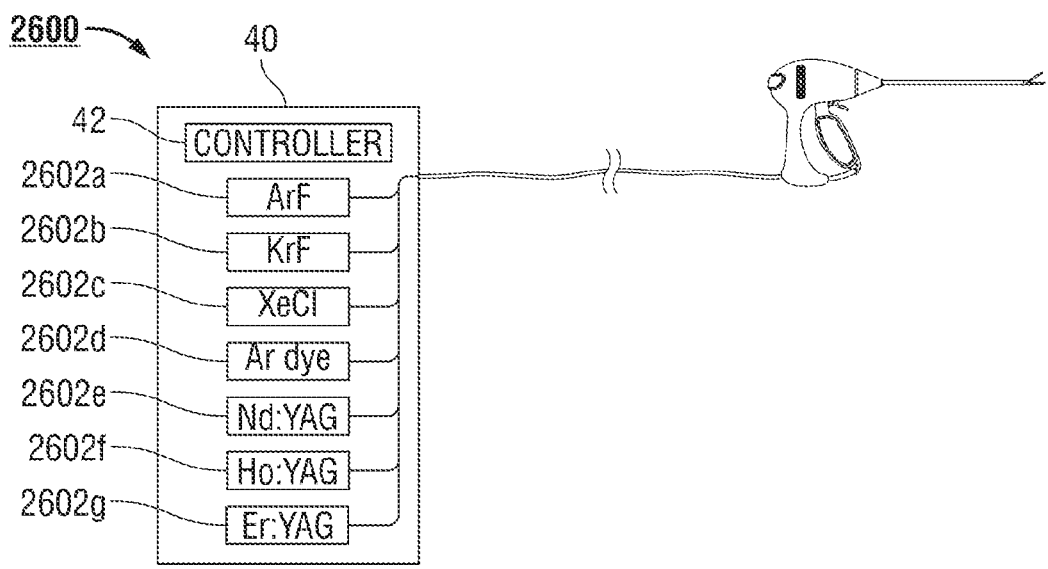
FIG. 25 is a schematic diagram of a surgical system according to the present disclosure.

FIG. 25 shows a light energy surgical system 2600 including the generator 40 and the forceps 10. The forceps 10 may include any of the embodiments of the jaw members described above. The generator 40 in combination with the forceps 10 may be utilized to generate light having a desired wavelength. The generator 40 may produce light energy at single or multiple wavelengths and may include a plurality of laser sources described above that are capable of producing light at multiple wavelengths. The generator 40 includes a plurality of laser light sources to generate laser light having a wavelength from about 100 nm to about 10,000 nm, which covers the majority of the tissue constituents. In particular, the generator 40 includes an ArF excimer laser 2602a, a KrF excimer laser 2602b, a XeCl excimer laser 2602c, an argon-dye laser 2602d, an Nd:YAG laser 2602e, an Ho:YAG laser 2602f, an Er:YAG laser 2602g.

Figure 26:
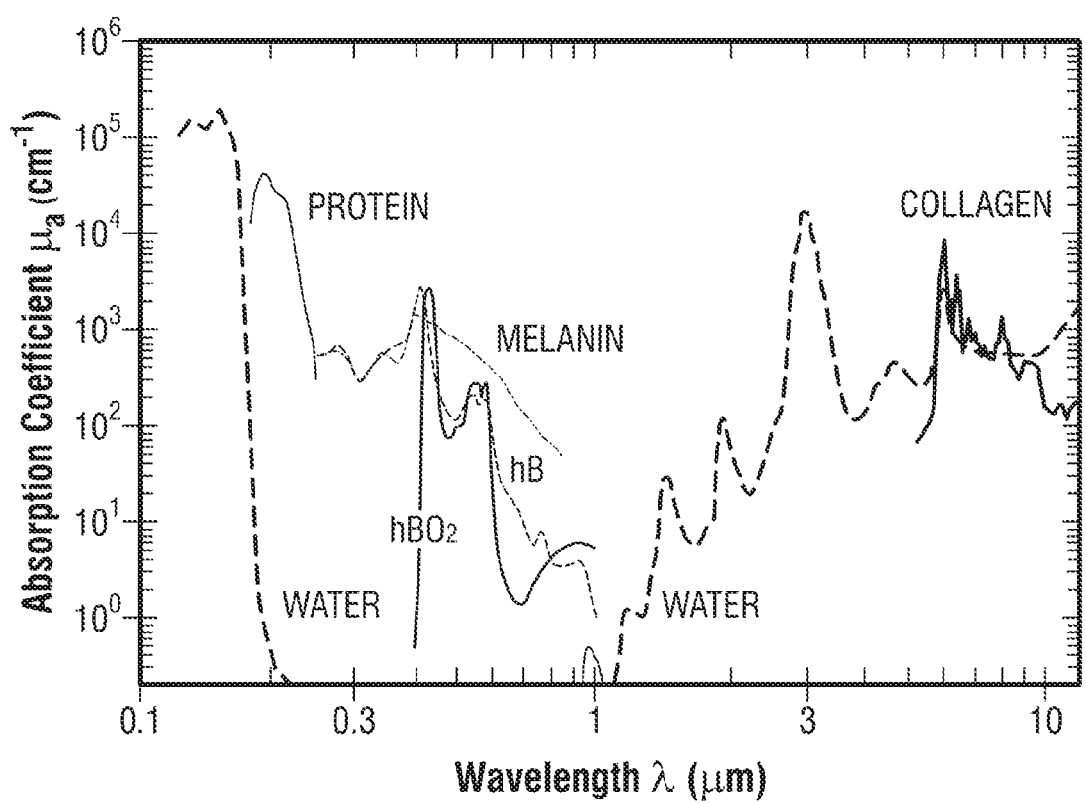
FIG. 26 is a plot of absorption coefficient versus wavelength of tissue constituents.
Figure 27:
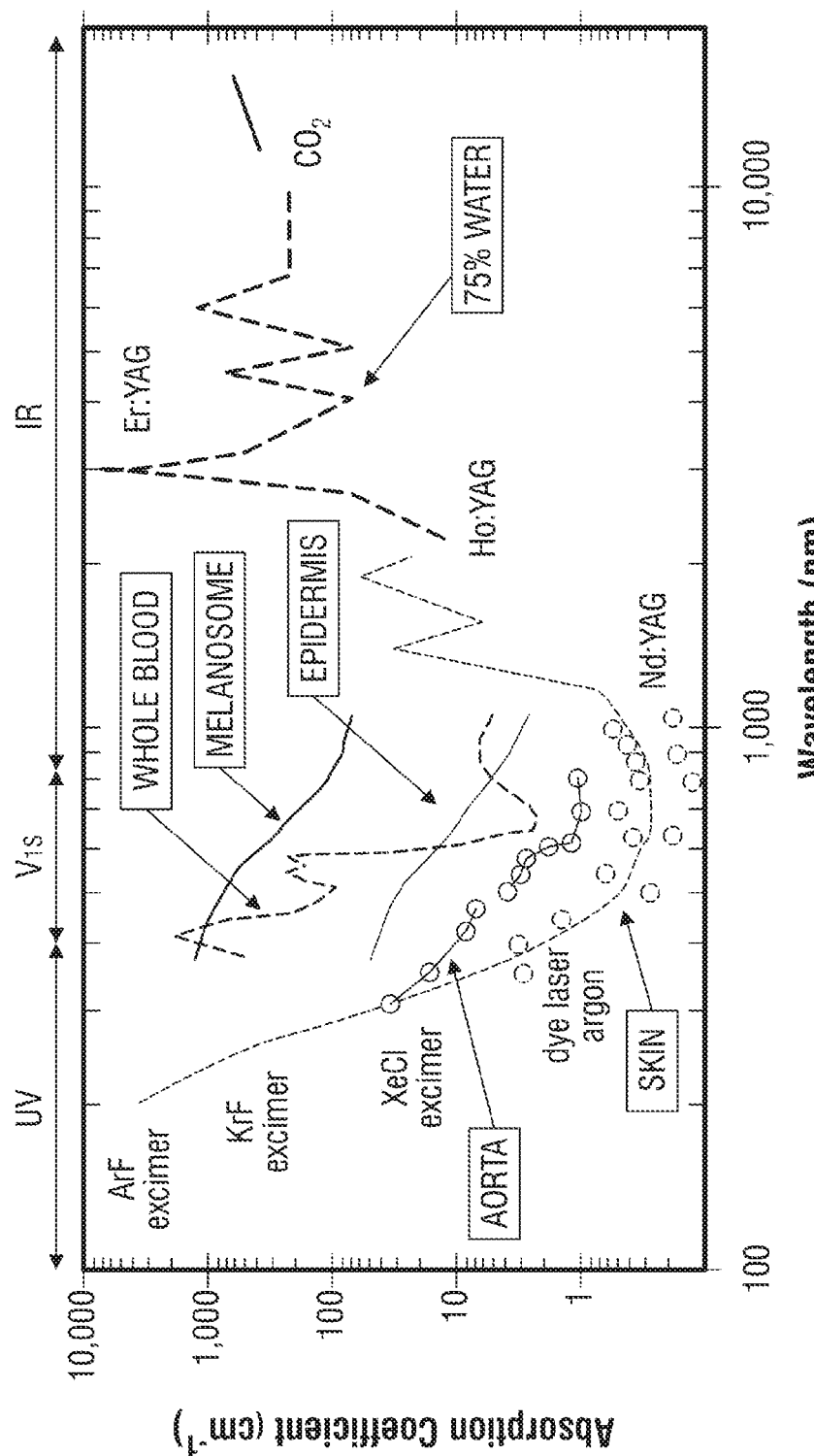
FIG. 27 is a plot of absorption coefficient versus wavelength of tissue constituents and laser light sources.

The forceps 10 may be used to determine condition and composition of tissue, as described in further detail above with respect to FIGS. 7A and 7B. FIG. 26 shows a graph illustrating absorption of various tissue constituents as a function of the wavelength ranging from ultraviolet (UV) spectrum to infrared (IR) spectrum. In particular, FIG. 27 also lists laser light sources 2602a-2602g provided in the generator 40 that generate light at the wavelengths that best match the absorption coefficient of the tissue constituents. Tissue constituents that are encountered in tissue include, but are not limited to water, vasculature, epidermis and other skin layers, whole blood, melanosome, collagen, and the like.

During operation, the forceps 10 is used to analyze tissue, including measuring the absorption thereof. The absorption measurements are analyzed by the controller 42 of the generator 40 which then determines which of the one or more laser light sources 2602a-2602g to activate to obtain optimal absorption of the light energy. The controller 42 may be coupled to a multiplexer (not shown) and/or another optical output switching apparatus to control activation of the laser light sources 2602a-2602g.

The forceps 10 may sense optical tissue properties continuously during the sealing procedure and to vary light energy output including intensity and which of the laser light sources 2602a-2602g are activated. Once it is determined that the sealing procedure is complete, the controller 42 may activate specific laser light sources 2602a-2602g most suitable for cutting sealed tissue.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end-effector assembly, comprising:
   first and second jaw members, each of the first and second jaw members including a sealing surface, at least one of the first or second jaw members movable from a first position wherein the jaw members are disposed in spaced relation relative to one another to a second position wherein the sealing surfaces cooperate to grasp tissue therebetween;
   at least one end-firing optical fiber operably disposed at a distal end of at least one of the first jaw member or the second jaw member;
   at least one side-firing optical fiber operably associated with at least one of the first jaw member or the second jaw member; and
   a two-stage switch including a first stage operably responsive to a first depression force and a second stage operably responsive to a second depression force greater than the first depression force, wherein actuation of the first stage corresponds to activation of the at least one side-firing optical fiber and actuation of the second stage corresponds to activation of the at least one end-firing optical fiber.

2. The end-effector assembly of claim 1, wherein the at least one end-firing optical fiber is configured to output light through a distal end of the at least one of the first jaw member or the second jaw member along a longitudinal axis defined by one of the at least one end-firing optical fibers.

3. The end-effector assembly of claim 1, wherein the at least one side-firing optical fiber is configured to output light along a plane perpendicular to a longitudinal axis defined by one of the at least one end-firing optical fibers.

4. A forceps, comprising:
   a housing;
   a shaft including a distal end and a proximal end and defining a longitudinal axis, the proximal end operatively coupled to the housing;
   an end-effector assembly coupled to the distal end of the shaft and including first and second jaw members, each of the first and second jaw members including a sealing surface, at least one of the first or second jaw members movable from a first position wherein the jaw members are disposed in spaced relation relative to one another to a second position wherein the sealing surfaces cooperate to grasp tissue therebetween;
   an end-firing optical fiber operably coupled to at least one of the first jaw member or the second jaw member and configured to emit light from a distal end of the at least one of the first jaw member or the second jaw member into tissue;
   a side-firing optical fiber operably associated with at least one of the first jaw member or the second jaw member; and
   a two-stage switch including a first stage operably responsive to a first depression force and a second stage operably responsive to a second depression force greater than the first depression force, wherein actuation of the first stage corresponds to activation of the side-firing optical fiber and actuation of the second stage corresponds to activation of the end-firing optical fiber.

5. The forceps of claim 4, wherein the end-firing optical fiber is configured to output light through the distal end of the at least one of the first jaw member or the second jaw member along the longitudinal axis.

6. The forceps of claim 4, wherein each of the first and second jaw members further includes an outer housing.

7. The forceps of claim 6, wherein the end-firing optical fiber is disposed at a distal end of one of the outer housings such that a distal end of the end-firing optical fiber is exposed through one of the outer housings.

* * * * *